United States Patent
Hachiya et al.

(10) Patent No.: US 9,491,411 B2
(45) Date of Patent: *Nov. 8, 2016

(54) ELECTRONIC COMPONENT MOUNTING APPARATUS AND ELECTRONIC COMPONENT MOUNTING METHOD

(71) Applicant: Panasonic Corporation, Osaka (JP)

(72) Inventors: Eiichi Hachiya, Yamanashi (JP); Takashi Nakamura, Yamanashi (JP); David L. Kelly, Ann Arbor, MI (US); Jose Camara, Ann Arbor, MI (US)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 497 days.

This patent is subject to a terminal disclaimer.

(21) Appl. No.: 13/950,531

(22) Filed: Jul. 25, 2013

(65) Prior Publication Data
US 2015/0029328 A1    Jan. 29, 2015

(51) Int. Cl.
H04N 9/47       (2006.01)
H04N 7/18       (2006.01)
H05K 13/08      (2006.01)
H04N 5/235      (2006.01)
G01N 21/956     (2006.01)

(52) U.S. Cl.
CPC .............. *H04N 7/18* (2013.01); *H05K 13/08* (2013.01); *G01N 21/956* (2013.01); *H04N 5/2354* (2013.01)

(58) Field of Classification Search
CPC ..................................... H05K 13/04
USPC .......................................... 348/87
See application file for complete search history.

(56) References Cited

U.S. PATENT DOCUMENTS

| | | |
|---|---|---|
| 5,999,640 A | 12/1999 | Hatase et al. |
| 6,144,452 A | 11/2000 | Hachiya |
| 6,211,958 B1 | 4/2001 | Hachiya et al. |
| 6,348,947 B1 | 2/2002 | Hatase |
| 2002/0031279 A1 | 3/2002 | Shimizu |
| 2007/0294875 A1* | 12/2007 | Hachiya ............. H05K 13/0413 29/428 |
| 2012/0233852 A1* | 9/2012 | Abe ................... H05K 13/0413 29/739 |

FOREIGN PATENT DOCUMENTS

| | | |
|---|---|---|
| JP | 07-151522 A | 6/1995 |
| JP | 08-255996 A | 10/1996 |
| JP | 2002-094296 A | 3/2002 |
| JP | 2002-107126 A | 4/2002 |
| JP | 3318146 B2 | 6/2002 |
| JP | 3336774 B2 | 8/2002 |
| JP | 3341569 B2 | 8/2002 |
| JP | 3578588 B2 | 7/2004 |
| JP | 2005-216933 A | 8/2005 |
| JP | 3893184 B2 | 12/2006 |
| JP | 2007-013021 A | 1/2007 |
| JP | 2010-016115 A | 1/2010 |

OTHER PUBLICATIONS

International Search Report for Application No. PCT/JP2014/000286 dated Apr. 8, 2014.

* cited by examiner

*Primary Examiner* — Hung Dang
*Assistant Examiner* — Girumsew Wendmagegn
(74) *Attorney, Agent, or Firm* — Pearne & Gordon LLP

(57) ABSTRACT

A control unit of an electronic component mounting apparatus controls a component imaging unit so as to move an electronic component that is held by the holding unit, when the holding unit is moved in a direction, which is oblique to a conveyance direction of a substrate and is close to the substrate, by a movement mechanism unit.

10 Claims, 30 Drawing Sheets

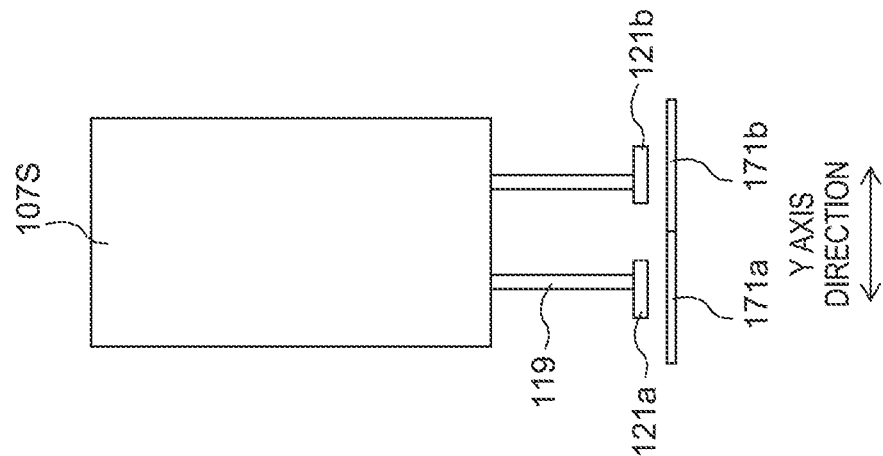
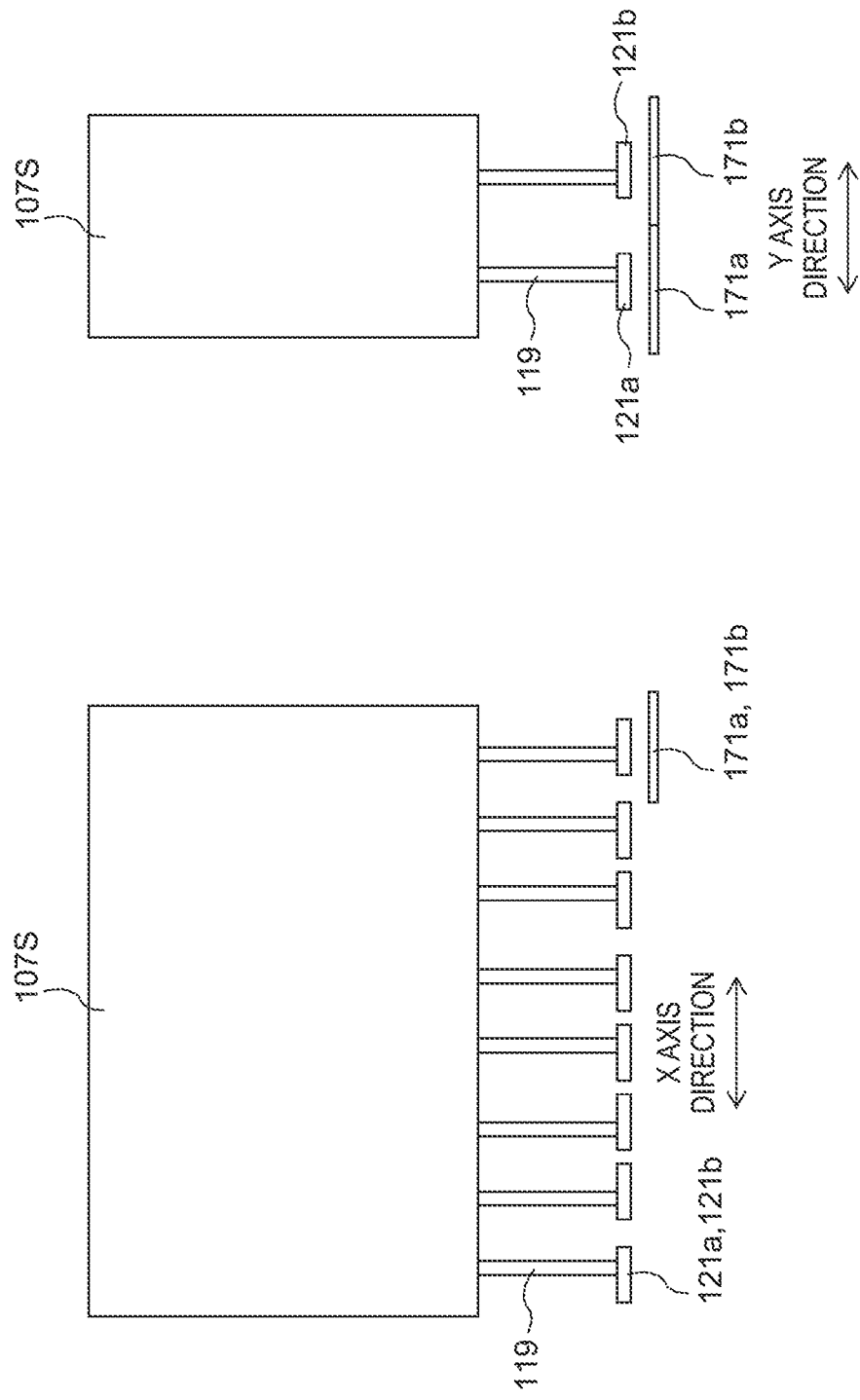

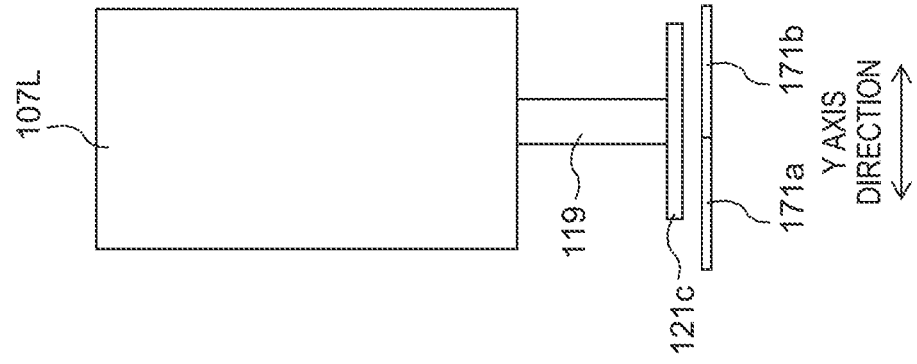
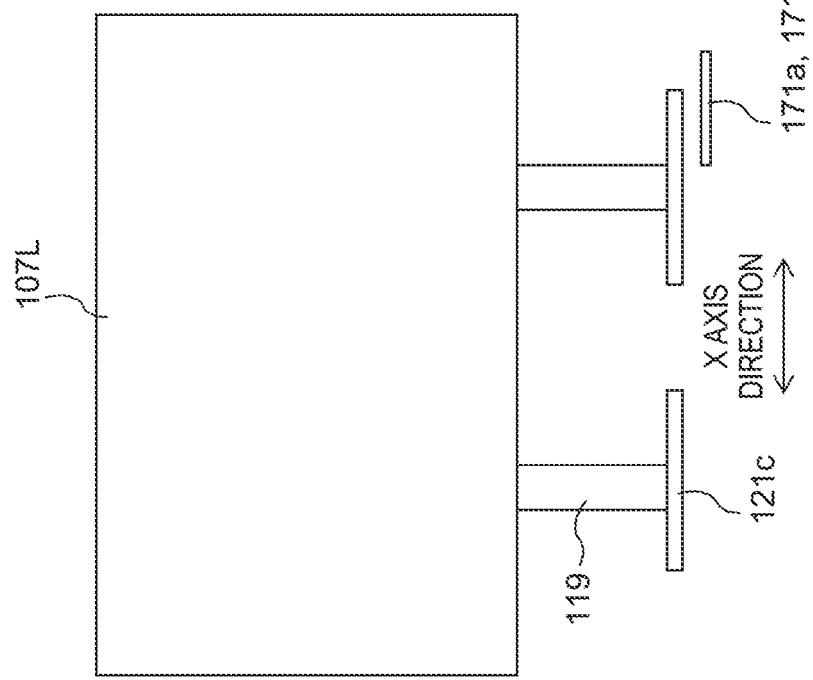

ELECTRONIC COMPONENT MOUNTING APPARATUS AND ELECTRONIC COMPONENT MOUNTING METHOD

BACKGROUND OF THE INVENTION

1. Field of the Invention

The present invention relates to an electronic component mounting apparatus and an electronic component mounting method for mounting electronic components onto a substrate.

2. Description of the Related Art

Most electronic component mounting apparatuses that are used currently image electronic components held by a mounting head so as to recognize holding positions of the electronic components or the like, before the mounting head mounts the electronic components picked up from a part feeder on a substrate. In addition, when imaging the electronic components, lighting is applied to the electronic components. Furthermore, as a camera used for imaging the electronic components, a line camera or a 2D camera is used.

Although the line camera can be used to from small electronic components to large electronic components, lighting thereof is limited. That is, it is impossible to switch the method to apply lighting to the electronic components in the process of single mechanical scanning using the line camera. For this reason, in order to apply lightings of different forms to one electronic component to obtain an image, there is a need for two or more mechanical scanning. Furthermore, in order to image a large electronic component using the line camera, there is a need for a number of imaging elements capable of covering a maximum length of the electronic component. However, the greater the number of imaging elements, the longer a scanning time of the line camera. For this reason, when using the line camera also available for a large electronic component, it takes time for single mechanical scanning, and thus a speed of taking the image is limited. Furthermore, a constant speed scanning is essential, and there is a need to scan the line camera in a direction perpendicular to a line of the imaging elements owing to one-dimensional scanning.

A plurality of imaging elements of different sizes is prepared for a 2D sensor, and the imaging elements used for imaging are switched depending on the sizes of the electronic components. However, a head of the 2D sensor does not correspond to a configuration of a two line nozzle. In order to correspond to the configuration of the two line nozzle, there is a need to prepare two imaging elements for a small electronic component and one imaging element for a large electronic component. That is, it is necessary to achieve a camera constituted by three imaging elements on the same visual field. According to the configuration, if the imaging element for the large electronic component is achieved by the imaging element arranged in a line form, the scanning time becomes a problem, and if the imaging element for the large electronic component is achieved by the imaging element arranged in an area form, the cost thereof and a reading time of image data become a problem.

In the conventional art, in component inspection using a three-dimensional image such as in coplanarity inspection of leads of a QFP (Quad Flat Package) in the electronic component mounting apparatus, a type using a laser beam and a position detection element (PSD) described in Japanese Patent No. 3578588 has been mainly used. This type is basically different from the type using the camera for imaging the two-dimensional image in methods of the lighting and the imaging. For this reason, when adopting the type using the two-dimensional image, since both means for two-dimensional imaging and means for three-dimensional imaging have been provided in the electronic component mounting apparatus, there has been a great demerit in view of a size and costs of the electronic component mounting apparatus. Furthermore, essentially, in order to measure heights of the electronic components through the irradiation of the laser beam, although there is a need for a mechanical operation of the laser beam using a polygon mirror, the scanning time of the laser beam is limited. For this reason, it has been unsuitable to apply the type using the laser beam and the PSD to a production line for a chip component such as a resistor or a capacitor that is required to be mass-produced and speeded up, or a production line in which a strict takt time is required.

As other conventional arts, there are Japanese Patent No. 3336774, Japanese Patent No. 3318146, Japanese Patent No. 3341569, and Japanese Patent No. 3893184.

SUMMARY OF THE INVENTION

An object of the present invention is to provide an electronic component mounting apparatus and an electronic component mounting method capable of shortening a movement time of the electronic component mounted on the substrate.

According to the present invention, there is provided an electronic component mounting apparatus which includes a substrate conveyance mechanism unit configured to convey a substrate with an electronic component mounted thereon in a first direction; a component supply unit configured to supply the electronic component; a holding unit configured to hold the electronic component supplied from the component supply unit; a movement mechanism unit configured to move the holding unit; a component imaging unit configured to image the electronic component that is held by the holding unit; a control unit configured to control an imaging form of the electronic component by the component imaging unit; and a component recognition unit configured to recognize the electronic component based on an image that is imaged by the component imaging unit, wherein the component imaging unit has an area camera that includes at least one imaging element, and the control unit controls the component imaging unit so as to image the electronic component that is held by the holding unit when the holding unit is moved in a direction oblique to the first direction and close to the substrate by the movement mechanism unit.

According to the present invention, there is provided an electronic component mounting apparatus which includes a substrate conveyance mechanism unit configured to convey a substrate with an electronic component mounted thereon in a first direction; a component supply unit configured to supply the electronic component; a holding unit configured to hold the electronic component supplied from the component supply unit; a movement mechanism unit configured to move the holding unit; a component imaging unit configured to image the electronic component that is held by the holding unit; a control unit configured to control an imaging form of the electronic component by the component imaging unit; and a component recognition unit configured to recognize the electronic component based on an image that is imaged by the component imaging unit, wherein the component imaging unit has at least three area cameras that include at least one imaging element, visual fields of the imaging element are common to each other regardless of the area cameras, and the control unit controls the component imaging unit so as to image the electronic component that is held by the holding unit when the holding unit is moved in a direction oblique to the first direction and close to the substrate by the movement mechanism unit.

According to the present invention, there is provided an electronic component mounting method performed by an electronic component mounting apparatus which includes a substrate conveyance mechanism unit configured to convey a substrate with an electronic component mounted thereon in a first direction; a component supply unit configured to supply the electronic component; a holding unit configured to hold the electronic component supplied from the component supply unit; a movement mechanism unit configured to move the holding unit; a component imaging unit configured to image the electronic component that is held by the holding unit; a control unit configured to control an imaging form of the electronic component by the component imaging unit; and a component recognition unit configured to recognize the electronic component based on an image that is imaged by the component imaging unit, the component imaging unit having at least three area cameras that include at least one imaging element, visual fields of the imaging element being common to each other regardless of the area camera, wherein the control unit controls the component imaging unit so as to image the electronic component that is held by the holding unit when the holding unit is moved in a direction oblique to the first direction and close to the substrate by the movement mechanism unit.

According to the electronic component mounting apparatus and the electronic component mounting method related to the present invention, it is possible to shorten the movement time of the electronic component mounted on the substrate.

BRIEF DESCRIPTION OF THE PREFERRED EMBODIMENTS

Figure 8:
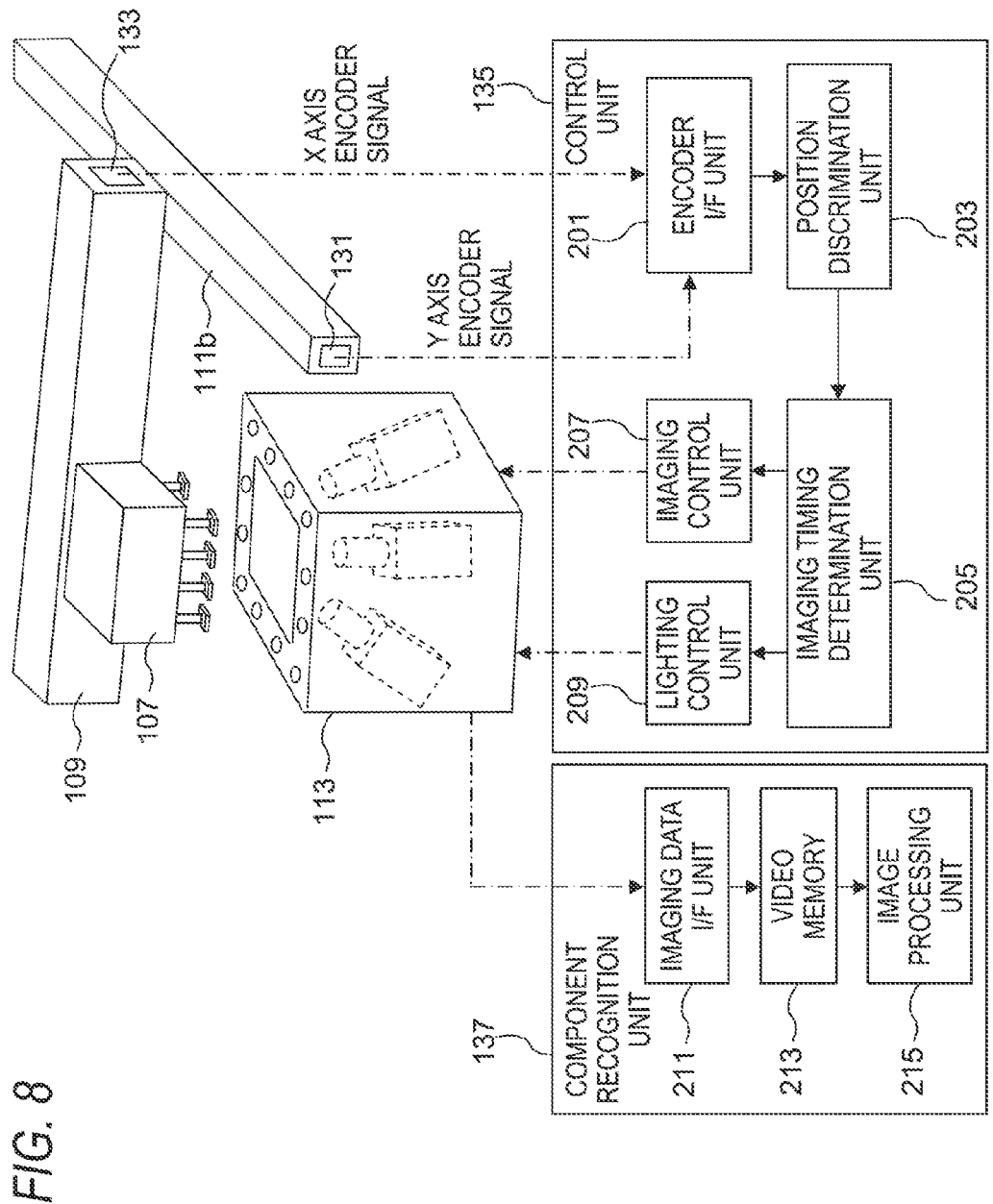

FIG. 8 is a diagram that illustrates a relationship between encoders 131 and 133, a control unit 135, a component recognition unit 137 and other constituents, and each internal configuration of the control unit 135 and the component recognition unit 137 in the electronic component mounting apparatus of an embodiment.

FIG. 9 is a diagram that illustrates a relationship between a configuration of a head portion 107S for a small electronic component and visual fields 171a and 171b of two imaging elements of each camera of the 3D sensor 113.

FIG. 10 is a diagram that illustrates a relationship between a configuration of the head portion 107S for a small electronic component and visual fields 171a and 171b of two imaging elements of each camera of the 3D sensor 113.

FIG. 11 is a diagram that illustrates a relationship between a configuration of a head portion 107L for a large electronic component and visual fields 171a and 171b of two imaging elements of each camera of the 3D sensor 113.

FIG. 12 is a diagram that illustrates a relationship between a configuration of the head portion 107L for the large electronic component and visual fields 171a and 171b of two imaging elements of each camera of the 3D sensor 113.

Figure 13:
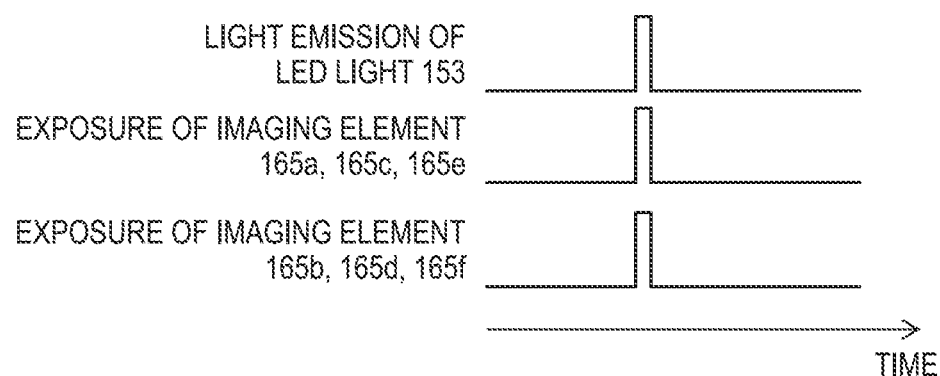

FIG. 13 is a diagram that illustrates an example of timing of exposure and lighting when the 3D sensor 113 images a small electronic component sucked to a head unit 107S of FIGS. 9 and 10.

Figure 14:
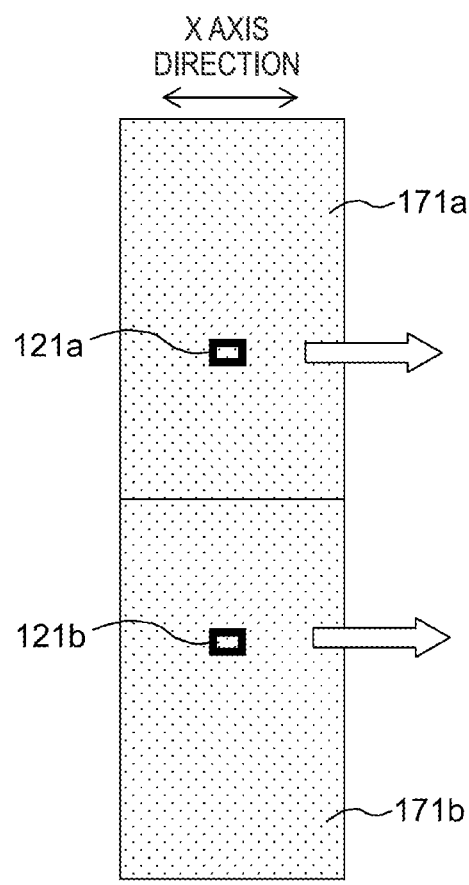

FIG. 14 is a diagram that illustrates a vertical positional relationship between the visual fields of each imaging element and the small electronic component when being imaged at the timing illustrated in FIG. 13.

Figure 15:
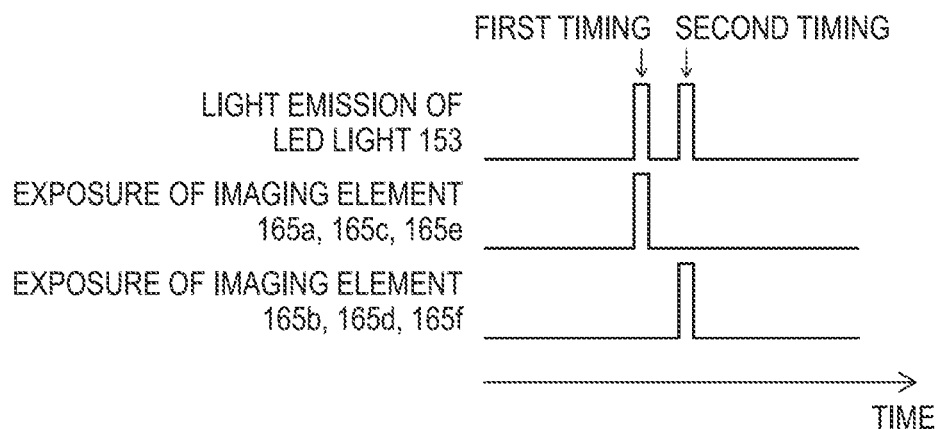

FIG. 15 is a diagram that illustrates another example of timing of exposure and lighting when the 3D sensor 113 images a small electronic component sucked to the head unit 107S of FIGS. 9 and 10.

Figure 16:
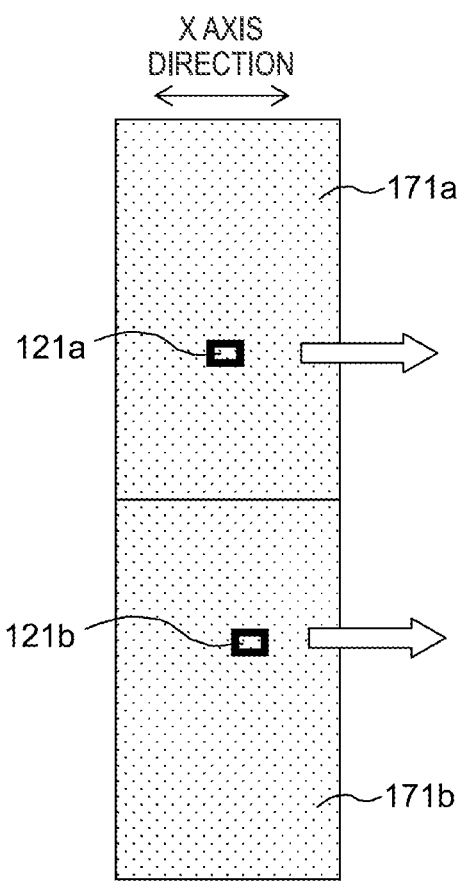

FIG. 16 is a diagram that illustrates a vertical positional relationship between the visual fields of each imaging element and the small electronic component when being imaged at the timing illustrated in FIG. 15.

Figure 17:
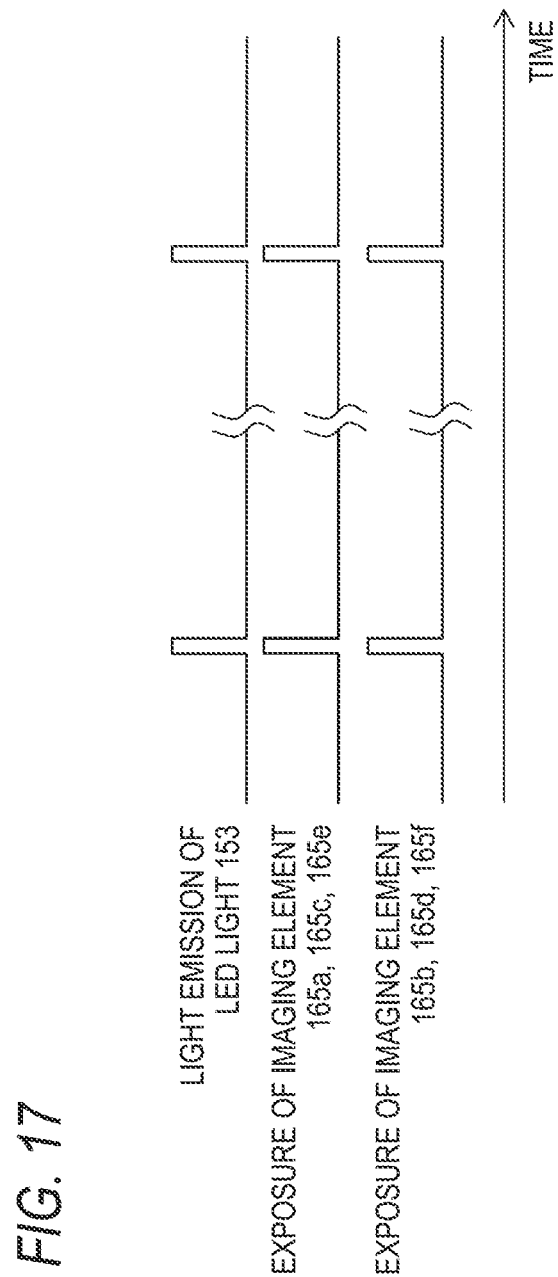

FIG. 17 is a diagram that illustrates an example of timing of exposure and lighting when the 3D sensor 113 images a large electronic component sucked to a head unit 107L of FIGS. 11 and 12.

Figure 18:
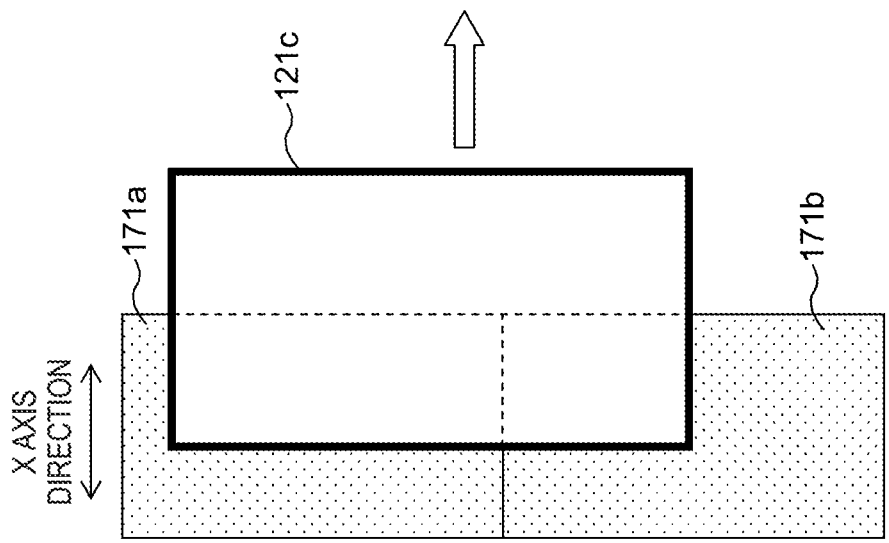

FIG. 18 is a diagram that illustrates a vertical positional relationship between the visual fields of each imaging element and the large electronic component when being initially imaged.

Figure 19:
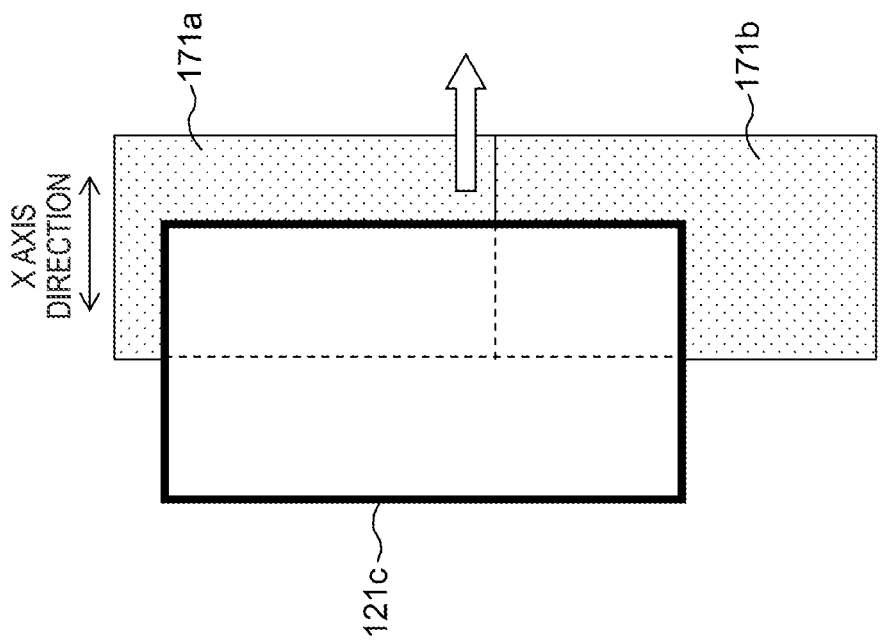

FIG. 19 is a diagram that illustrates a vertical positional relationship between the visual fields of each imaging element and the large electronic component when being imaged later.

Figure 20:
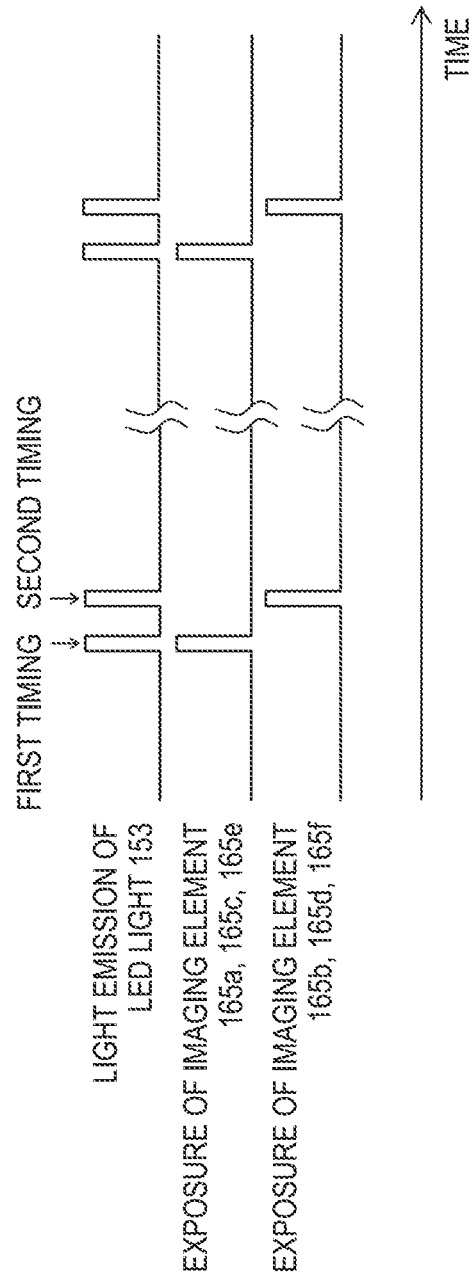

FIG. 20 is a diagram that illustrates another example of timing of exposure and lighting when the 3D sensor 113 images a large electronic component sucked to the head unit 107L of FIGS. 11 and 12.

Figure 21:
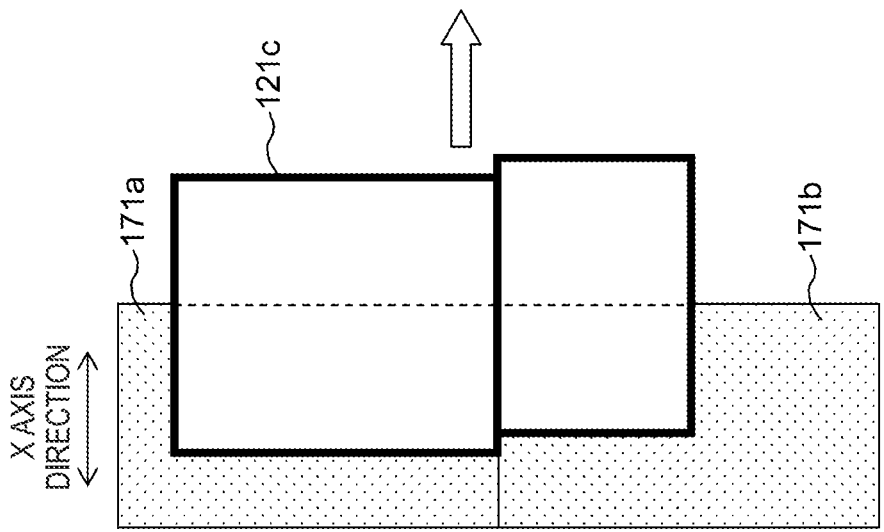

FIG. 21 is a diagram that illustrates a vertical positional relationship between the visual fields of each imaging element and the large electronic component when being initially imaged at the different timings.

Figure 22:
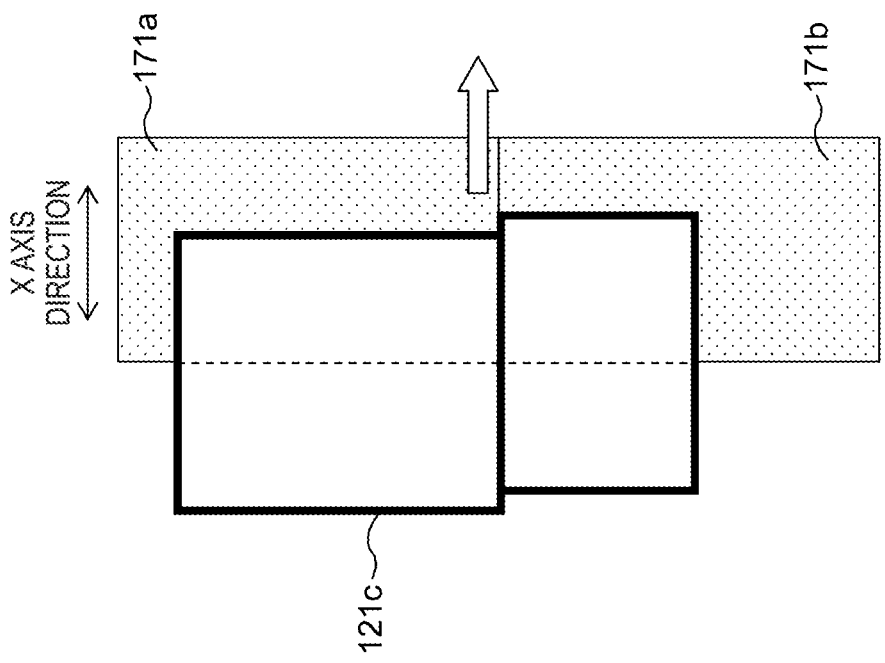

FIG. 22 is a diagram that illustrates a vertical positional relationship between the visual fields of each imaging element and the large electronic component when being imaged later at the different timings.

Figure 23:
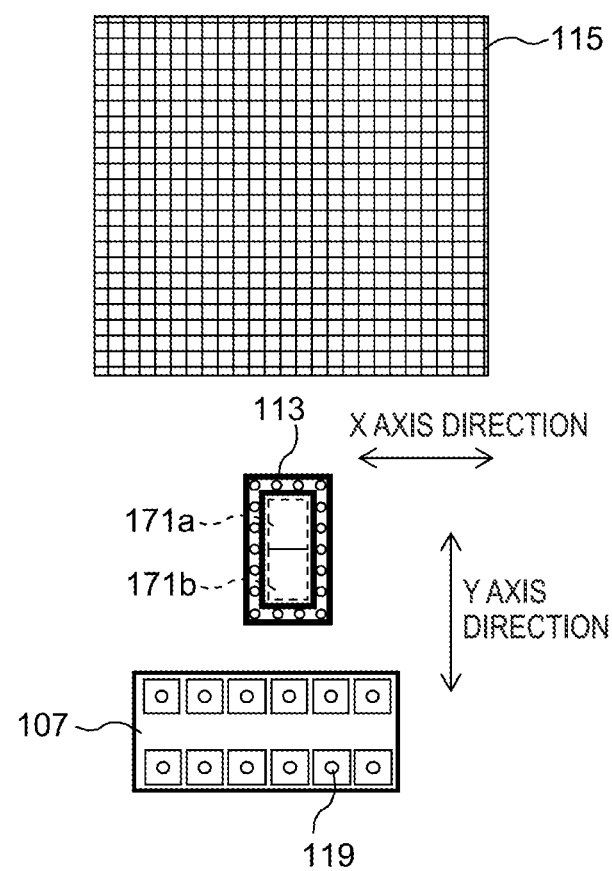

FIG. 23 is a diagram that illustrates an example of a horizontal positional relationship between the head unit 107 with nozzles 119 placed in two lines, the 3D sensor 113 and the substrate 115 with the electronic components mounted thereon.

Figure 24:
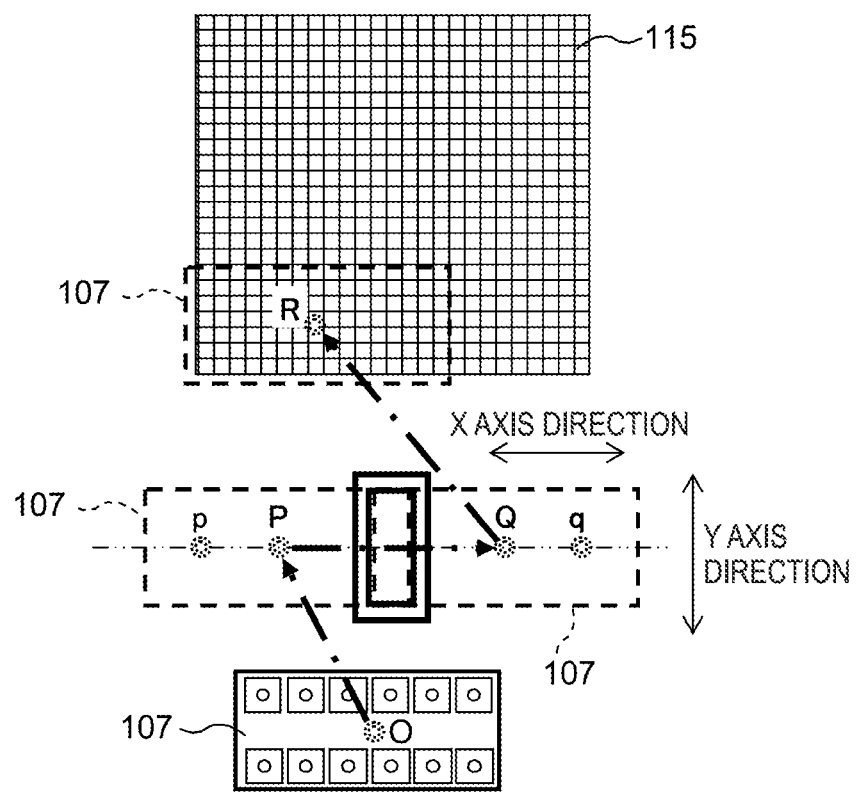

FIG. 24 is a diagram that illustrates a movement route in a second example until the head unit 107 sucks the electronic components from a feeder unit 103 and mounts the electronic components on the substrate 115.

Figure 25:
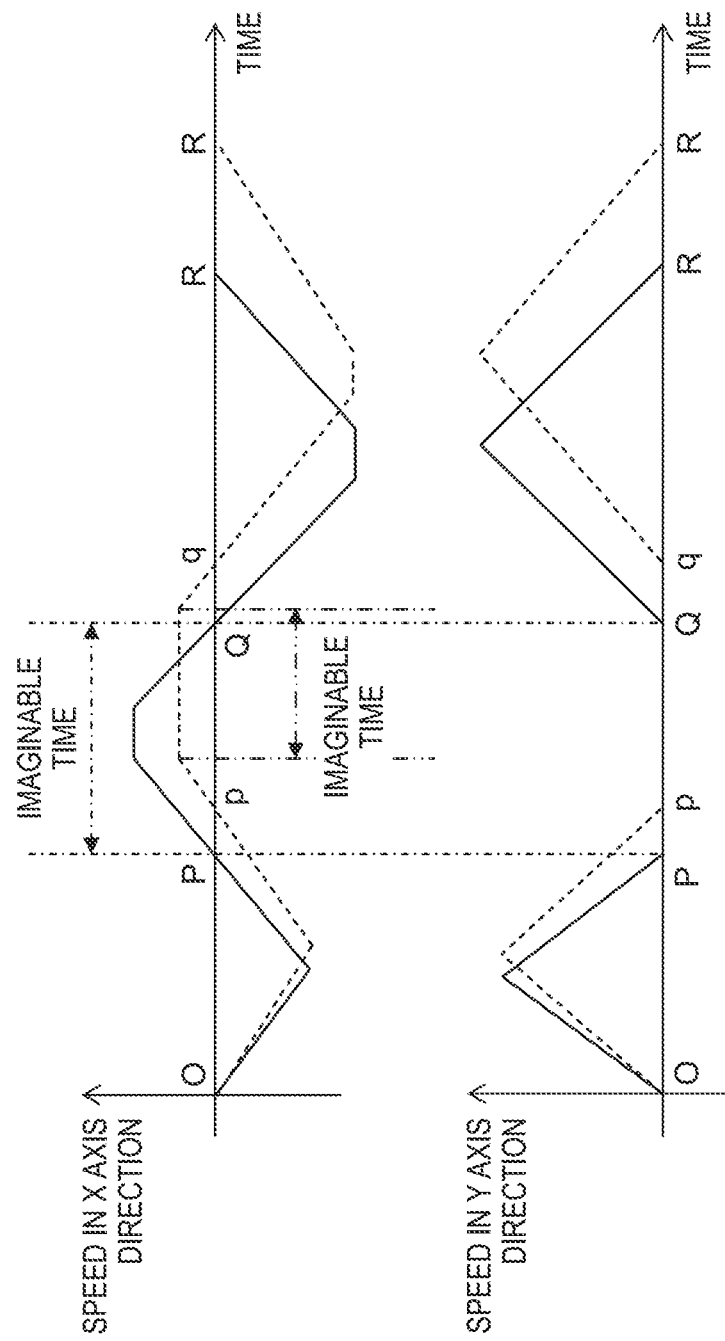

FIG. 25 is a diagram that illustrates a variation with time of a speed in an X axis direction and a speed in a Y axis direction when the head unit 17 illustrated in FIG. 23 is moved.

Figure 26:
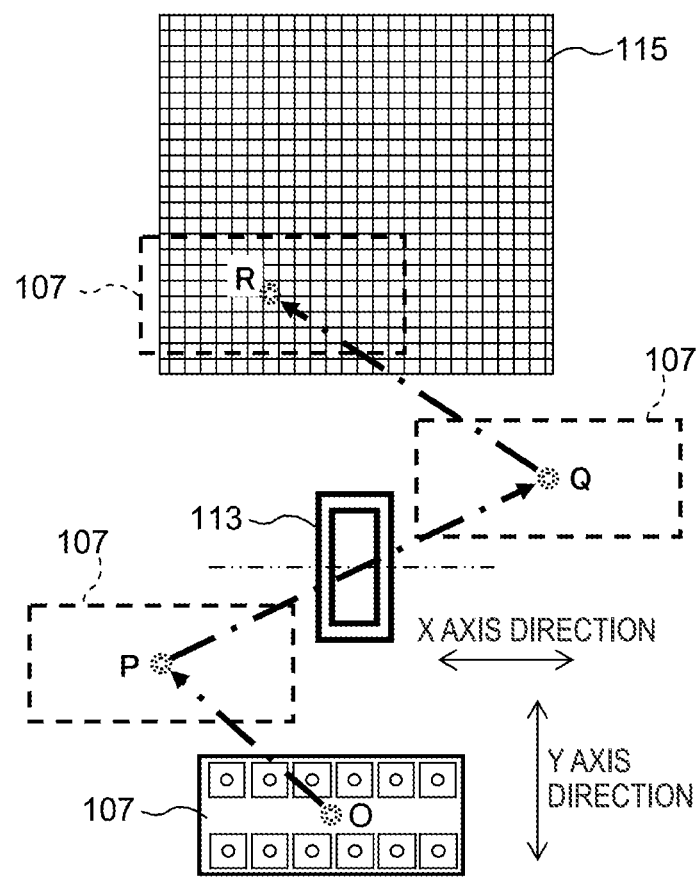

FIG. 26 is a diagram that illustrates a movement route in a third embodiment until the head unit 107 sucks the electronic components from the feeder unit 103 and mounts the electronic components on the substrate 115.

Figure 27:
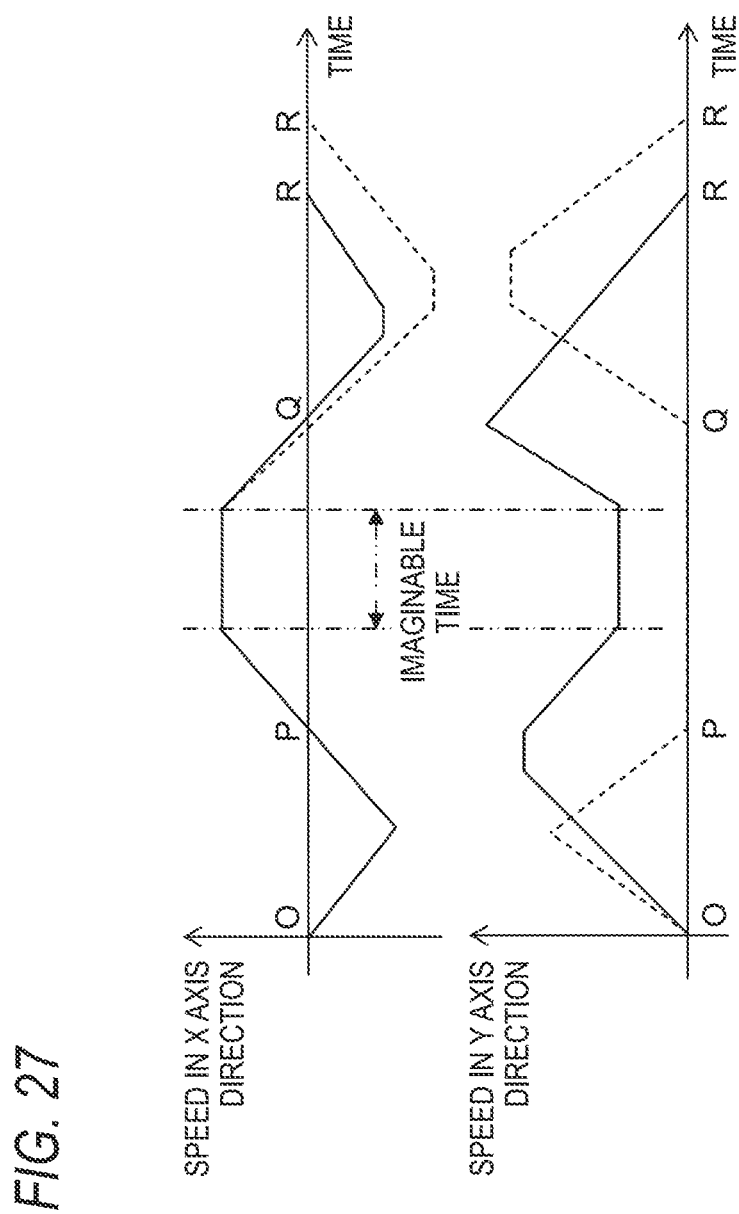

FIG. 27 is a diagram that illustrates a variation with time of a speed in an X axis direction and a speed in a Y axis direction when the head unit 17 illustrated in FIG. 26 is moved.

Figure 28:
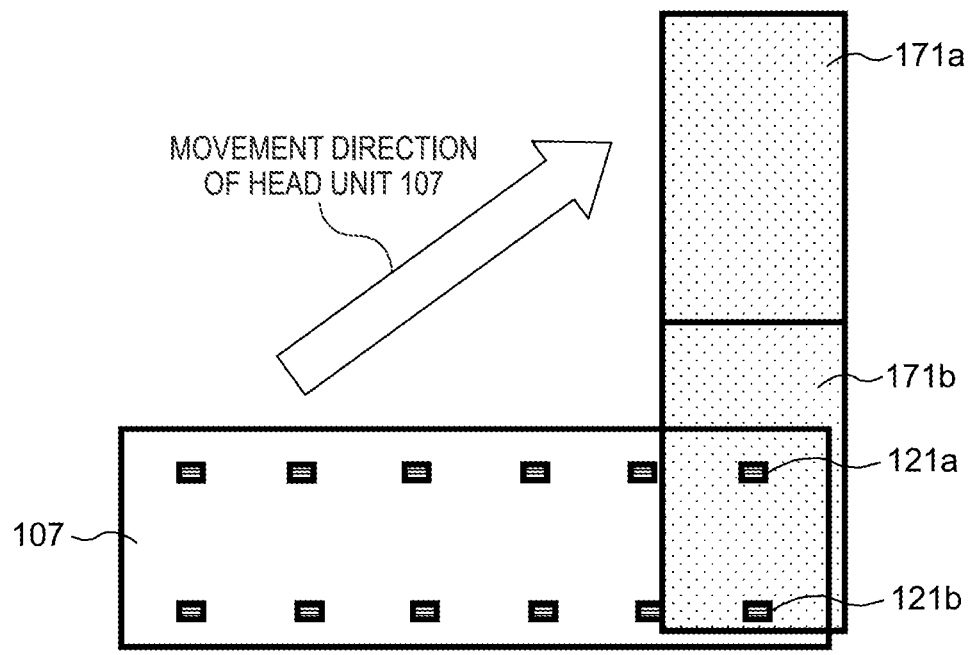

FIG. 28 is a diagram that illustrates a vertical positional relationship between visual fields 171a and 171b and the head unit 107 at the time of the first imaging timing of the electronic component using the 3D sensor 113.

Figure 29:
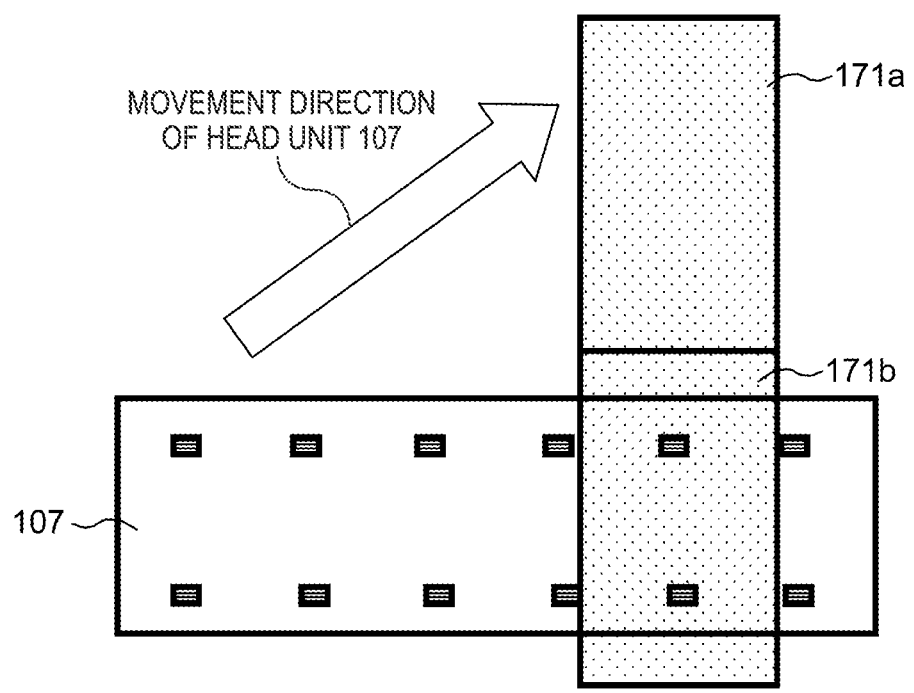

FIG. 29 is a diagram that illustrates a vertical positional relationship between visual fields 171a and 171b and the head unit 107 at the time of the second imaging timing of the electronic component using the 3D sensor 113.

Figure 30:
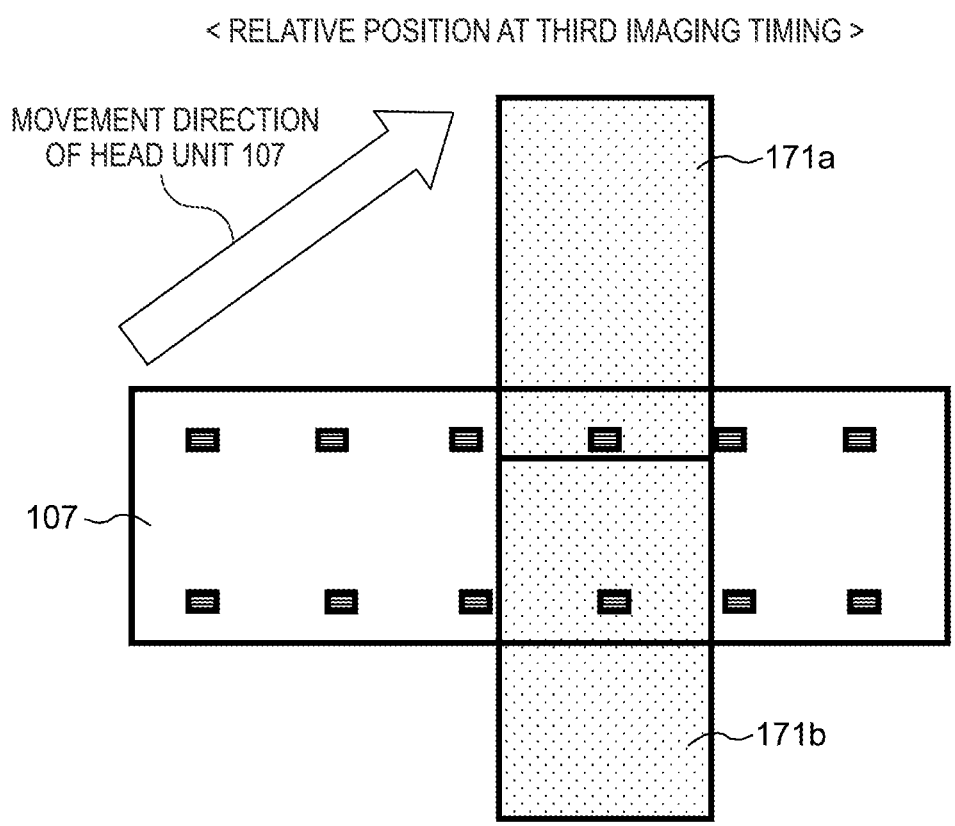

FIG. 30 is a diagram that illustrates a vertical positional relationship between visual fields 171a and 171b and the head unit 107 at the time of the third imaging timing of the electronic component using the 3D sensor 113.

Figure 31:
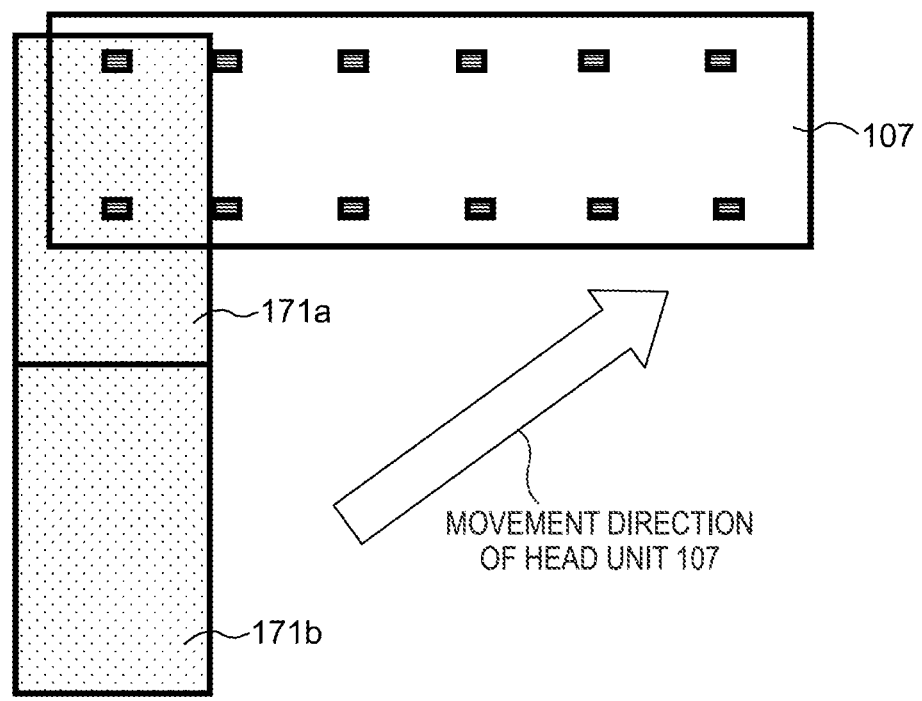

FIG. 31 is a diagram that illustrates a vertical positional relationship between visual fields 171a and 171b and the head unit 107 at the time of the sixth imaging timing of the electronic component using the 3D sensor 113.

Figure 32:
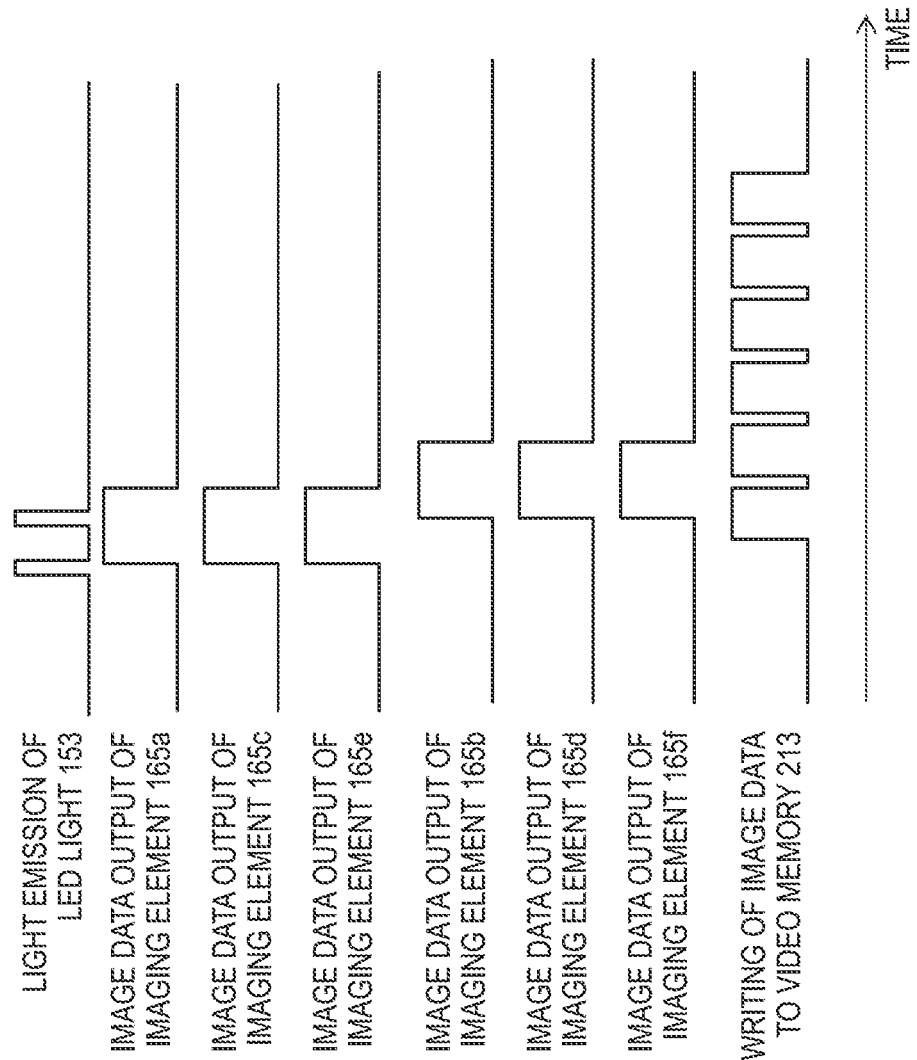

FIG. 32 is a diagram that illustrates each timing of the light emission of an LED light 153, the output of the image data of the imaging element, and writing of the image data to a video memory 213 when recognizing the electronic component sucked to the head unit 107 based on a three-dimensional image.

Figure 33:
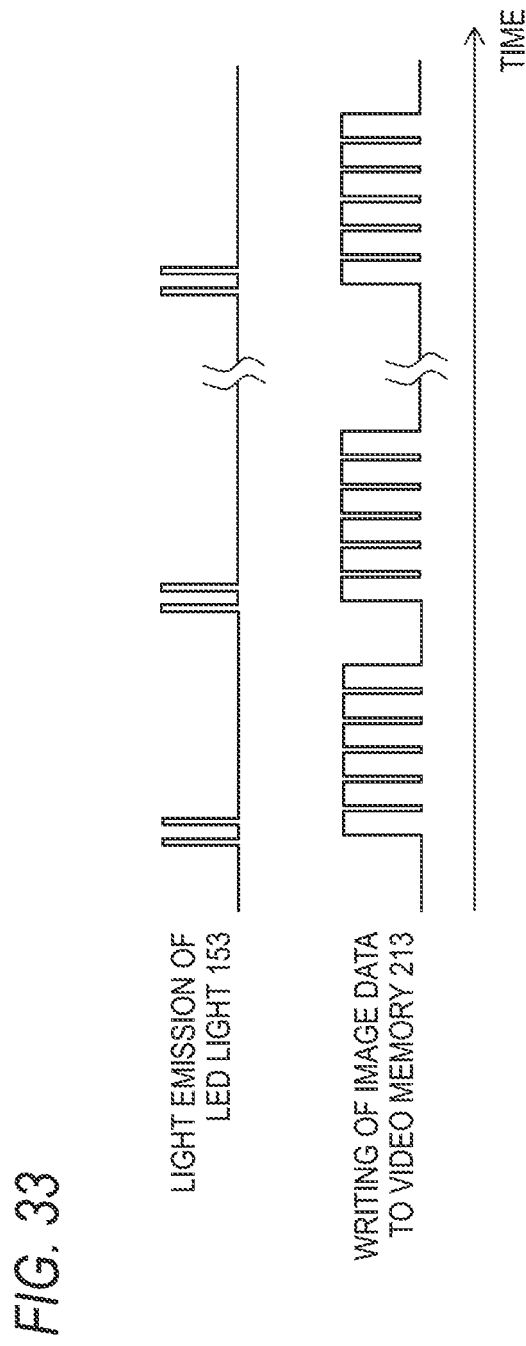

FIG. 33 is a diagram that illustrates each timing of the light emission of the LED light 153 and writing of the image data to the video memory 213 when the head unit 107 is moved in the X axis direction and the operations of FIG. 32 are performed several times.

Figure 34:
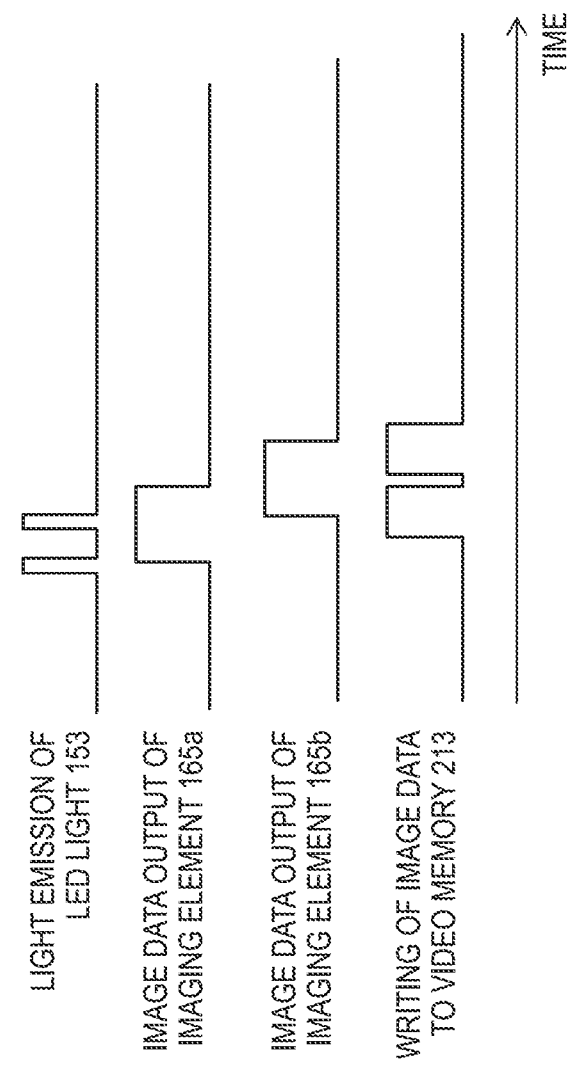

FIG. 34 is a diagram that illustrates each timing of the light emission of the LED light 153, the output of the image data of the imaging element, and writing of the image data to the video memory 213 when recognizing the electronic component sucked to the head unit 107 based on a two-dimensional image.

Figure 35:
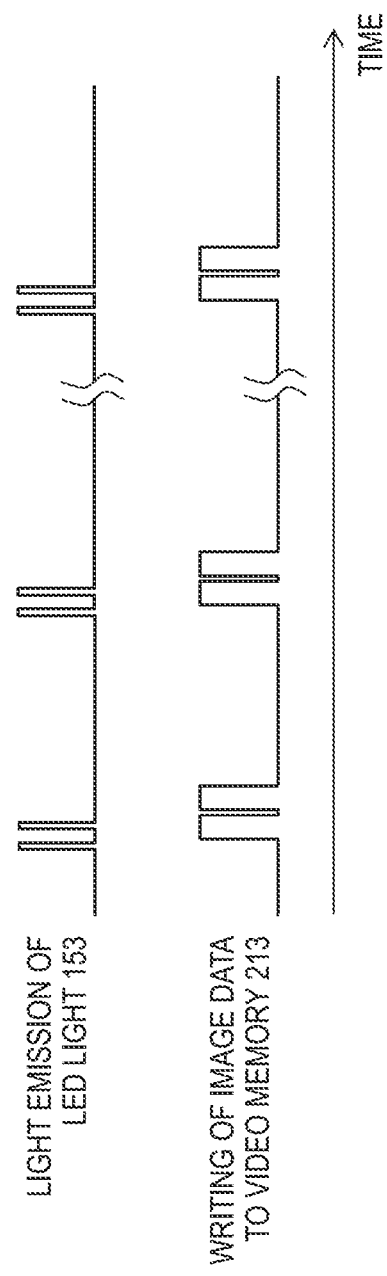

FIG. 35 is a diagram that illustrates each timing of the light emission of the LED light 153 and writing of the image data to the video memory 213 when the head unit 107 is moved in the X axis direction and the operation of FIG. 34 is performed several times.

Figure 36:
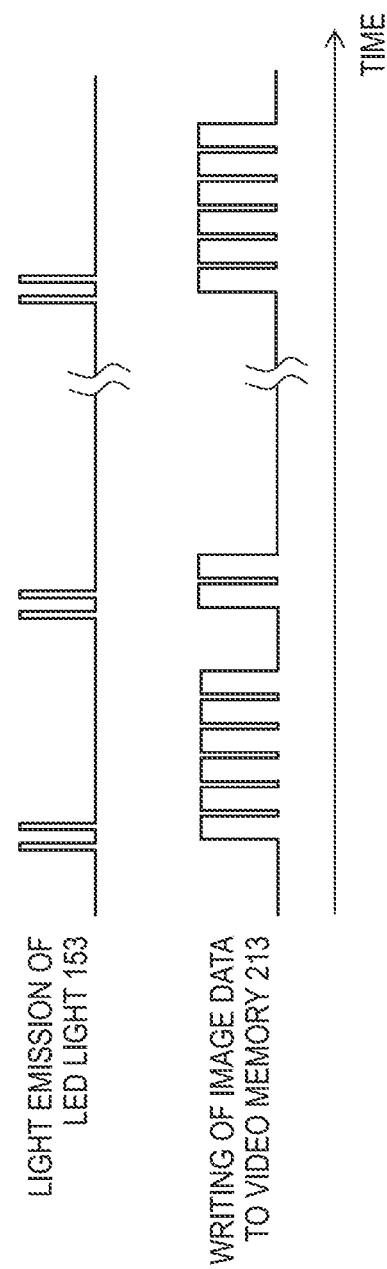

FIG. 36 is a diagram that illustrates an example of each timing of the light emission of the LED light 153 and writing of the image data to the video memory 213 when the head unit 107 is moved in the X axis direction and the operation illustrated in FIG. 32 or the operation illustrated in FIG. 35 is selectively performed.

DESCRIPTION OF THE PREFERRED EMBODIMENTS

Hereinafter, an embodiment of the present invention will be described with reference to the drawings.

An electronic component mounting apparatus of an embodiment related to the present invention mounts relatively small electronic components such as a resistor or a capacitor and relatively large electronic components such as a packaged LSI or a memory onto a print substrate or a substrate of a liquid crystal display panel or a plasma display panel. In the electronic component mounting apparatus, the electronic components are imaged before mounting the electronic components on the substrate, the positioning and a required inspection of the electronic components are performed by software processing using the imaged image, and then the electronic components are mounted on the substrate.

Figure 1:
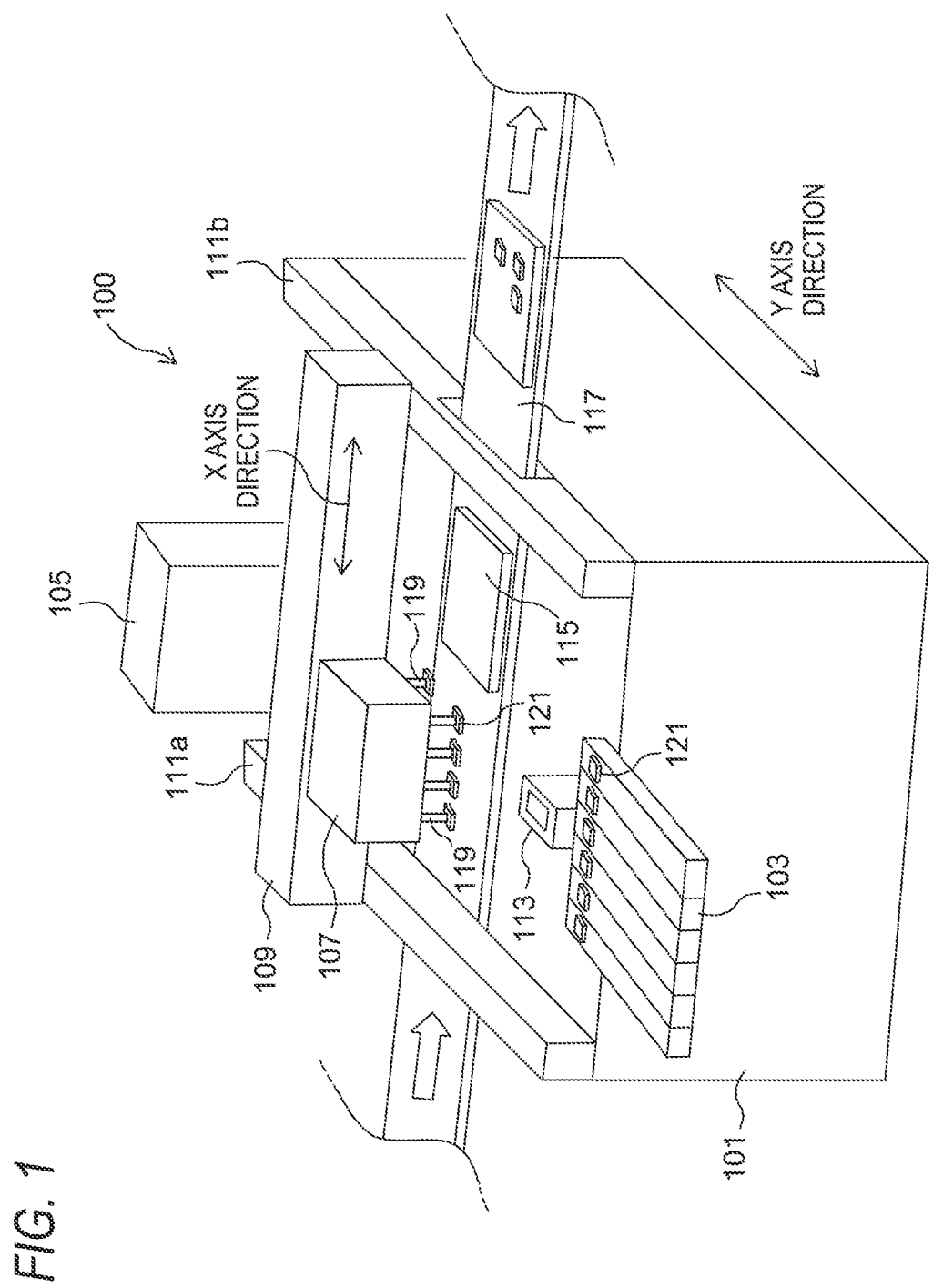
FIG. 1 is an overall perspective view of an electronic component mounting apparatus of an embodiment related to the present invention.
Figure 2:
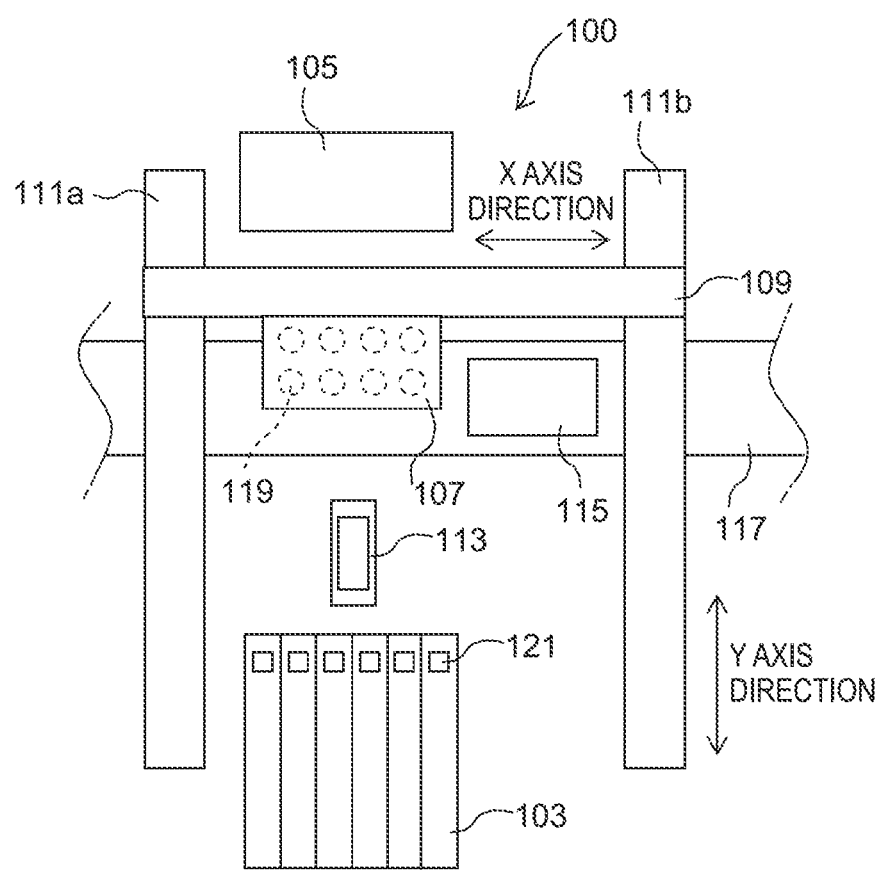
FIG. 2 is a top view of the electronic component mounting apparatus illustrated in FIG. 1.

FIG. 1 is an overall perspective view of the electronic component mounting apparatus of an embodiment related to the present invention. Furthermore, FIG. 2 is a top view of the electronic component mounting apparatus illustrated in FIG. 1. An electronic component mounting apparatus 100 of the present embodiment includes a main body 101, a feeder unit 103, a tray supply unit 105, a head unit 107, an X axis robot 109, Y axis robots 111a and 111b, and a three-dimensional sensor (hereinafter, referred to as a "3D sensor") 113. In addition, a belt 117 with the substrate 115 mounted thereon passes through the electronic component mounting apparatus 100.

The feeder unit 103 supplies a relatively small electronic component. The tray supply unit 105 supplies a relatively large electronic component. The head unit 107 has a plurality of nozzles 119 disposed in a matrix form on a bottom surface thereof. The head unit 107 holds electronic components 121 supplied from the feeder unit 103 or the tray supply unit 105 by sucking the electronic components 121 to the nozzle 119. In addition, the head unit 107 having the different numbers or forms of the nozzles 119 is used depending on the sizes or the kinds of the sucked electronic components. The X axis robot 109 moves the head unit 107 in an X axis direction illustrated in FIG. 1. The Y axis robots 111a and 111b move the head unit 107 in a Y axis direction illustrated in FIG. 1. The X axis is perpendicular to the Y axis. The 3D sensor 113 images the electronic component 121 to which the head unit 107 is sucked when the head unit 107 is moved by the X axis robot 109 or the Y axis robots 111a and 111b, from the lower side thereof.

Figure 3:
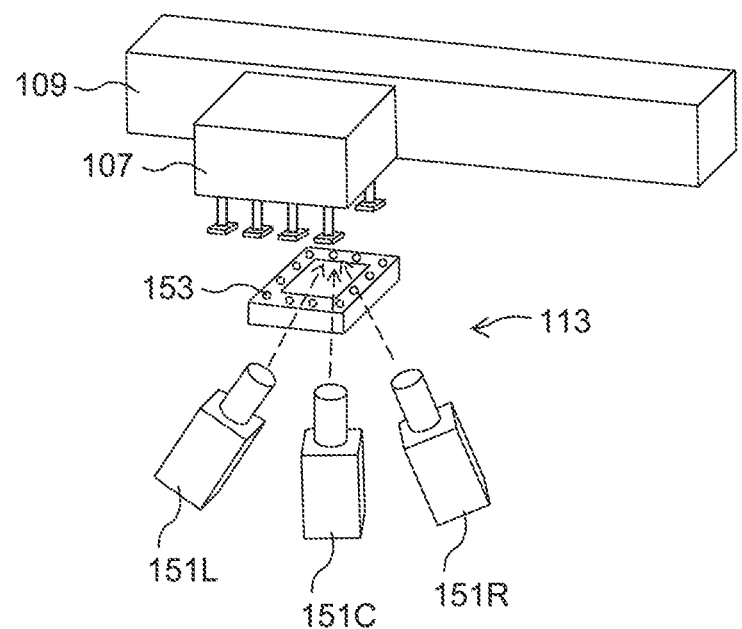
FIG. 3 is a schematic configuration diagram of a 3D sensor 113.

FIG. 3 is a schematic configuration diagram of the 3D sensor 113. As illustrated in FIG. 3, a center camera 151C configured to image the electronic component from just below the electronic component, and a left camera 151L and a right camera 151R configured to each image the same electronic component from a substantially symmetrical and oblique direction are provided inside the 3D sensor 113. In addition, focal positions of the center camera 151C, the left camera 151L and the right camera 151R are identical, and each camera has a function of an electronic shutter. Furthermore, a plurality of LED lights 153 as lighting means configured to light the electronic component from plural directions when imaging the electronic component are disposed in the 3D sensor 113.

Figure 4:
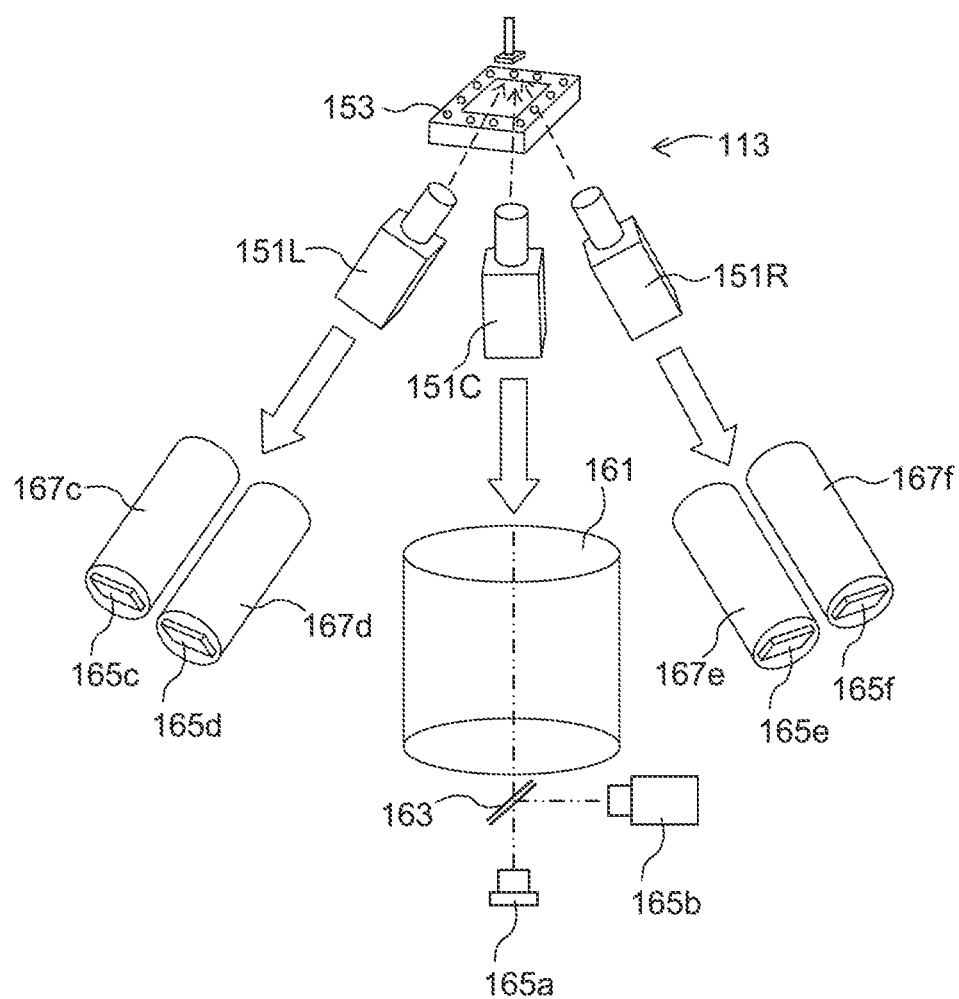
FIG. 4 is a diagram that describes the configuration and the operation of each camera included in the 3D sensor 113.

FIG. 4 is a diagram that describes the configuration and the operation of each camera included in the 3D sensor 113. As illustrated in FIG. 4, the center camera 151C, and the left camera 151L and the right camera 151R each have a group of imaging elements. In the center camera 151C, a beam splitter 163 is attached to one telecentric lens 161, and two imaging elements 165a and 165b each have a two-dimensional visual field. Furthermore, in the left camera 151L, lenses 167c and 167d are provided in each of the two imaging elements 165c and 165d. Similarly, in the right camera 151R, lenses 167e and 167f are provided in each of two imaging elements 165e and 165f. In addition, the visual field of the imaging element 165a of the center camera 151C is substantially common to the visual field of the imaging element 165c of the left camera 151L and the visual field of the imaging element 165e of the right camera 151R. In addition, the respective visual fields of the imaging element 165c of the left camera 151L and the imaging element 165e of the right camera 151R are also common to each other. Similarly, the visual field of the imaging element 165b of the center camera 151C is substantially common to the visual field of the imaging element 165d of the left camera 151L and the imaging element 165f of the right camera 151R. In addition, the respective visual fields of the imaging element 165d of the left camera 151L and the imaging element 165f of the right camera 151R are also common to each other.

Figure 5:
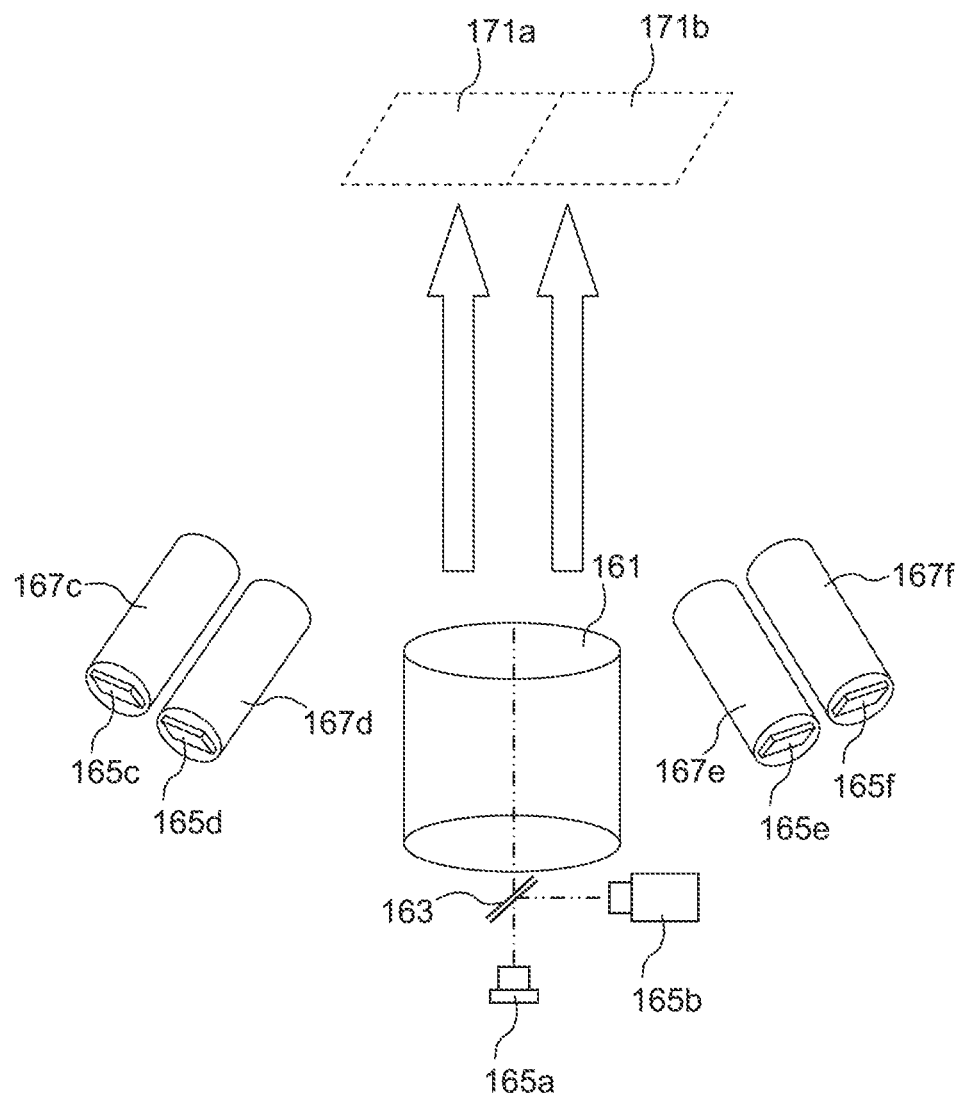
FIG. 5 is a diagram that describes the operation of a center camera 151C.

FIG. 5 is a diagram that describes the operation of the center camera 151C. As illustrated in FIG. 5, in the center camera 151C, the imaging element 165a images the visual field 171a and the imaging element 165b images the visual field 171b via the beam splitter 163 and the telecentric lens 161a. The respective regions of the visual fields 171a and 171b are greater than the size of the small electronic component when viewed from an imaging direction. In addition, the imaging elements 165a and 165b are each an independent device, and are also able to image the visual field at the same timing and to image the visual field at individual timings.

Figure 6:
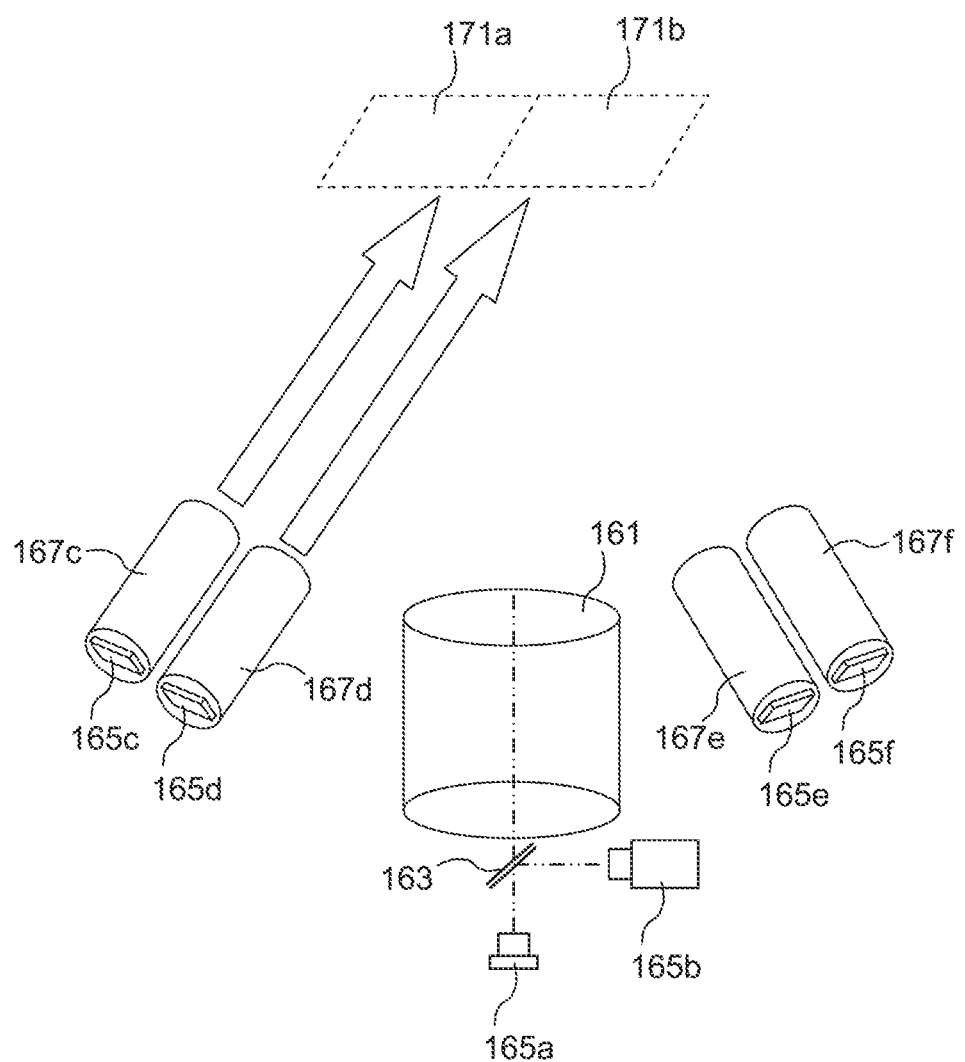
FIG. 6 is a diagram that describes the operation of a left camera 151L.

FIG. 6 is a diagram that describes the operation of the left camera 151L. As illustrated in FIG. 6, in the left camera 151L, the imaging element 165c images the visual field 171a via the lens 167c and the imaging element 165d images the visual field 171b via the lens 167d. In addition, the imaging elements 165c and 165d are each an independent device, and are also able to image the visual field at the same timing and to image the visual field at individual timings.

Figure 7:
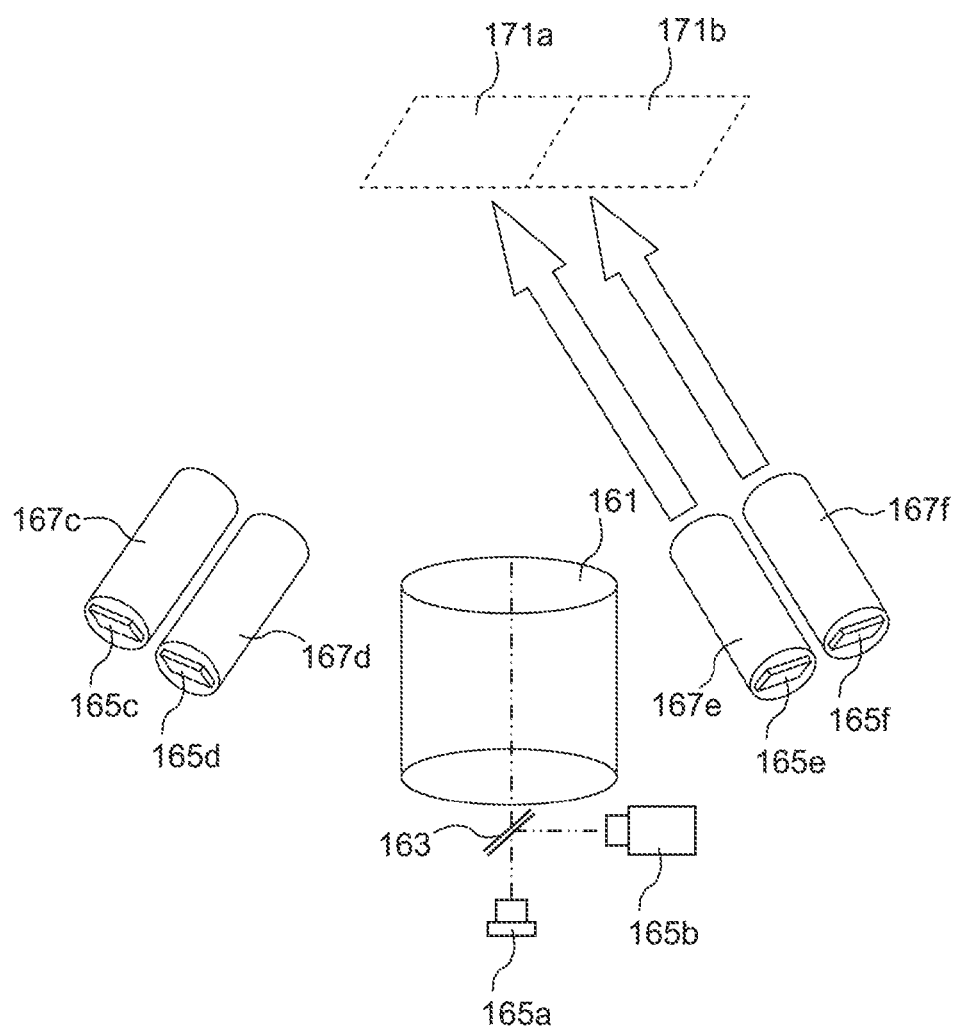
FIG. 7 is a diagram that describes the operation of a right camera 151R.

FIG. 7 is a diagram that describes the operation of the right camera 151R. As illustrated in FIG. 7, in the right camera 151R, the imaging element 165e images the visual field 171a via the lens 167e and the imaging element 165f images the visual field 171b via the lens 167f. In addition, the imaging elements 165e and 165f are each an independent device, and are also able to image the visual field at the same timing and to image the visual field at individual timings.

The electronic component mounting apparatus 100 of the present embodiment also includes an encoder, a control unit and a component recognition unit (not illustrated) in addition to the constituents illustrated in FIGS. 1 and 2. FIG. 8 is a diagram that illustrates a relationship between the encoders 131 and 133, the control unit 135, the component recognition unit 137 and other constituents, and each internal configuration of the control unit 135 and the component recognition unit 137 in the electronic component mounting apparatus of one embodiment.

The encoder 131 measures the movement of the head unit 107 in the X axis direction using the X axis robot 109 to output the signal (hereinafter, referred to as an "X axis encoder signal") that indicates an amount of movement of the head unit 107 in the X axis direction. Furthermore, the encoder 133 measures the movement of the head unit 107 in the Y axis direction using the Y axis robot 111 to output a signal (hereinafter, referred to as a "Y axis encoder signal") that indicates the movement of the head unit 107 in the Y axis direction. The control unit 135 controls the imaging timing of the imaging element of each camera which configures the 3D camera 113, and the light-up timing, the lighting form of the LED light 153 or the like, based on each signal that is output from the encoders 131 and 133 depending on the size of the electronic component to which the head unit 107 is sucked. The component recognition unit 137 recognizes the form of the electronic component or the like to which the head unit 107 is sucked, based on the image that is imaged by the 3D sensor 113.

As illustrated in FIG. 8, the control unit 135 has an encoder I/F unit 201, a position discrimination unit 203, an imaging timing determination unit 205, an imaging control unit 207, and a light control unit 209. The encoder I/F unit 201 receives the X axis encoder signal that is output from the encoder 131 and the Y axis encoder signal that is output from the encoder 133. The position discrimination unit 203 discriminates the position of the head unit 107, based on the X axis encoder signal and the Y axis encoder signal received by the encoder I/F unit 201. The imaging timing determination unit 205 determines the imaging timing using the 3D sensor 113 depending on the size and the kind of the electronic component sucked by the head unit 107, based on the position of the head unit 107. The imaging control unit 207 controls the exposure of the imaging elements of each camera of the 3D sensor 113, based on the imaging timing determined by the imaging timing determination unit 205. In addition, the imaging control unit 207 independently controls two imaging elements of each camera, respectively. The lighting control unit 209 controls the light emission of the LED light 153 of the 3D sensor 113, based on the imaging timing determined by the imaging timing determination unit 205. It is possible to change brightness of light irradiated to the electronic component, an irradiation angle or the kind of the lighting (for example, transmission lighting and a reflected lighting) through the light emission control of the LED light 153 using the lighting control unit 209.

As illustrated in FIG. 8, the component recognition unit 137 has an image data I/F unit 211, a video memory 213, and an image processing unit 215. The image data I/F unit 211 receives the data of the image that is imaged by the imaging elements of each camera of the 3D sensor 113. The image data received by the image data I/F unit 211 is stored in the video memory 213. The image processing unit 215 performs the image processing using the image data stored in the video memory 213 depending on the kind of the electronic component to be recognized. In addition, the image processing unit 215 may process the image using only the image data from the center camera 151C of the 3D sensor 113. In this case, although the obtained image is a two-dimensional image, the processing time of the image processing unit 215 can be shortened. Furthermore, when the image processing unit 215 process the image using image data from each of all the cameras (the center camera 151C, the left camera 151L and the right camera 151R) of the 3D sensor 113, a three-dimensional image without a dead angle is obtained.

FIGS. 9 and 10 are drawings that illustrate a relationship between the configuration of the head unit 107S for the small electronic component and the visual fields 171a and 171b of two imaging elements of each camera of the 3D sensor 113. FIG. 9 is a side view of the head unit 107S when viewing the head unit 107S from the Y axis direction, and FIG. 10 is a side view of the head unit 107S when viewing the head unit 107S from the X axis direction. It is preferable that there be a number of electronic components capable of being mounted on the substrate by a series of operations such as the adsorption, the recognition, and the mount of the electronic components as one of the functions of the electronic component mounting apparatus, without being limited to the electronic component mounting apparatus of the present embodiment. For this reason, the configuration of the head unit 107S illustrated in FIGS. 9 and 10 in which the nozzles 119 are placed in two lines is effective in that many small electronic components can be sucked. In the head unit 107S illustrated in FIGS. 9 and 10, nozzles 119 are arranged in two lines in the Y axis direction so that eight nozzles 119 are arranged for each line, and each nozzle sucks one small electronic component. When the small electronic component is mounted on the head unit 107S, two electronic components 121a and 121b sucked to two nozzles 119 disposed in the Y axis direction are each individually included in each visual field of two imaging elements of each camera of the 3D sensor 113.

FIGS. 11 and 12 are diagrams that illustrate the relationship between the configuration of the head unit 107L for the large electronic component and the visual fields 171a and 171*b* of two imaging elements of each camera of the 3D sensor 113. FIG. 11 is a side view of the head unit 107L when viewing the head unit 107L from the Y axis direction, and FIG. 12 is a side view of the head unit 107L when viewing the head unit 107L from the X axis direction. When mounting the large electronic component that does not come into a visual field of one imaging element, for example, the head unit 107L illustrated in FIGS. 11 and 12 is used. In the head unit 107L illustrated in FIGS. 11 and 12, nozzles 119 are arranged in a line in the Y axis direction so that two nozzles 119 are arranged for each line, and each nozzle sucks one large electronic component 121*c*. When the large electronic component 121*c* is mounted on the head unit 107L, only a part of the electronic components 121*c* is included in each visual field of two imaging elements of each camera of the 3D sensor 113. Furthermore, all the electronic components 121*c* are not imaged in one imaging using two imaging elements. For this reason, imaging is performed several times after moving the head unit 107L in the X axis direction.

FIRST EXAMPLE

In order to achieve the effective takt time in the electronic component mounting apparatus of the present embodiment, optimization of the imaging operation of the electronic components is important. That is, if the head unit 107 does not reciprocate when imaging the electronic components, the head unit 107 only passes through the 3D sensor 113 once to achieve an image required for the recognition of the electronic components regardless of the sizes of the electronic components, the effective takt time is achieved. Hereinafter, the imaging of the electronic components controlled by the imaging control unit 207 and the lighting control unit 209 of the control unit 135 included in the electronic component mounting apparatus of the present embodiment will be described.

FIG. 13 is a diagram that illustrates an example of the timing of the exposure and the lighting when the 3D sensor 113 images the small electronic component sucked to the head unit 107S of FIGS. 9 and 10. Furthermore, FIG. 14 is a diagram that illustrates a vertical positional relationship between the visual field of each imaging element and the small electronic component when imaging the electronic component at the timing illustrated in FIG. 13. In the examples illustrated in FIGS. 13 and 14, the small electronic components 121*a* and 121*b* are each imaged at the same timing and under the same lighting. In addition, the imaging surface of the electronic component 121*a* located inside the visual field 171*a* is imaged by the imaging elements 165*a*, 165*c* and 165*e*, and the imaging surface of the electronic component 121*b* located inside the visual field 171*b* is imaged by the imaging elements 165*b*, 165*d* and 165*f*. Thus, the component recognition unit 137 included in the electronic component mounting apparatus of the present embodiment is able to recognize the small electronic component from one image that is imaged by the imaging element corresponding to one visual field.

FIG. 15 is a diagram that illustrates another example of the timing of the exposure and the lighting when the 3D sensor 113 images the small electronic component sucked to the head unit 107S of FIGS. 9 and 10. Furthermore, FIG. 16 is a diagram that illustrates a vertical positional relationship between the visual field of each imaging element and the small electronic component when imaging the electronic component at the timing illustrated in FIG. 15. When the kinds of the small electronic components sucked by the head unit 107S in which the nozzles 119 are constituted in two lines are different for each line, the effective image is obtained by changing the lighting form of the LED light 153 for each kind of electronic component. For example, when imaging the electronic component sucked to the nozzles of one line, the lighting is relatively light, and when imaging the electronic component sucked to the nozzles of the other line, the lighting is relatively dark. For this reason, in the examples illustrated in FIGS. 15 and 16, the imaging timings of the small electronic components 121*a* and 121*b* are each delayed, and the respective lighting timings are set to the different lighting forms. That is, the imaging surface of the electronic component 121*a* located inside the visual field 171*a* is imaged by the imaging elements 165*a*, 165*c* and 165*e* at the first timing under the first lighting, and the imaging surface of the electronic component 121*b* located inside the visual field 171*b* is imaged by the imaging elements 165*b*, 165*d* and 165*f* at the second timing under the second lighting.

In addition, an interval on the X axis between the position of the electronic component 121*a* when being imaged at the first timing and the position of the electronic component 121*b* when being imaged at the second timing, that is, a movement distance on the X axis of the head unit 107S is very small. For example, if the light emission time of the LED light 153 is 10 µs, and the movement distance on the X axis of the head unit 107S is 2000 mm/second, the interval is 20 µm.

FIG. 17 is a diagram that illustrates another example of the timing of the exposure and the lighting when the 3D sensor 113 images the large electronic component sucked to the head unit 107L of FIGS. 11 and 12. Furthermore, FIG. 18 is a diagram that illustrates a vertical positional relationship between the visual field of each imaging element and the large electronic component when being initially imaged. FIG. 19 is a diagram that illustrates a vertical positional relationship between the visual field of each imaging element and the large electronic component when being imaged next. In the examples illustrated in FIGS. 17 to 19, after the large electronic component 121*c* crossing two visual fields 171*a* and 171*b* sucked to the head unit 107L, in which the nozzles 119 are constituted in a line, is imaged by the imaging element corresponding to each visual field at the same timing and under the same lighting, when the head unit 107L is moved by a predetermined length in the X axis direction, the imaging is performed again under the same conditions as those of the previous imaging time. Thus, the image processing unit 215 combines a plurality of images using the imaging elements corresponding to each visual field obtained by the imaging of several times, thereby to generate the image in which all imaging surfaces of the large electronic component 121*c* are included. Furthermore, the component recognition unit 137 is able to recognize the large electronic component from the image in which images of the plurality of images are combined by the image processing unit 215. In addition, the processing of combining images of the plurality of images are performed by any one of a method carried out by software configured to take data of each image to the video memory 213 once, and a method carried out by hardware in real time. The processing of the image processing unit 215 by any one method may be determined by a balance between the processing time and the processing capability.

FIG. 20 is a diagram that illustrates another example of the timing of the exposure and the lighting when the 3D sensor 113 images the large electronic component sucked to the head unit 107L of FIGS. 11 and 12. Furthermore, FIG.

21 is a diagram that illustrates a vertical positional relationship between the visual field of each imaging element and the large electronic component when being initially imaged at the different timings. FIG. 22 is a diagram that illustrates a vertical positional relationship between the visual field of each imaging element and the large electronic component when being imaged at the different timings next. In the examples illustrated in FIGS. 20 to 22, after the imaging surface of the large electronic component 121c is imaged by the imaging element corresponding to each visual field at different timings and under the same lighting, when the head unit 107L is moved by a predetermined length in the X axis direction, the imaging is performed again under the same conditions as those of the previous imaging time. In the case, if combining the images using the imaging element corresponding to each visual field obtained by the imaging of several times, the image processing unit 215 is also able to obtain the images of all imaging surfaces of the large electronic component 121c. In addition, since the imaging mode illustrated in FIG. 20 can be used together with the imaging mode illustrated in FIG. 15, the circuit design is more or less simple.

As mentioned above, in the first example, when recognizing the small electronic component coming into the visual field of one imaging element, an image is used which is imaged by one imaging element, and when recognizing the large electronic component exceeding two visual fields, an image is used in which the respective images imaged by two imaging elements corresponding to two visual fields are combined. Thus, the head unit 107 does not reciprocate, and the head unit 107 only passes through the 3D sensor 113 once to achieve an image required for the recognition of the electronic components regardless of the sizes of the electronic components. As a result, it is possible to recognize the electronic component to be inspected with a high speed and a high accuracy regardless of the sizes of the electronic components mounted on the substrate.

SECOND EXAMPLE

FIG. 23 is a diagram that illustrates an example of a horizontal positional relationship between the head unit 107 with the nozzles 119 placed in two lines, the 3D sensor 113 and the substrate 115 with the electronic components mounted thereon. Furthermore, FIG. 24 illustrates a movement route in a second example until the head unit 107 sucks the electronic components from the feeder unit 103 and mounts the electronic components onto the substrate 115. An O point illustrated in FIG. 24 indicates a central position of the head unit 107 when sucking the electronic components. The head unit 107 sucks the electronic components at the O point and then is moved to a P point by the X axis robot 109 and the Y axis robots 111a and 111b. Next, the head unit 107 is moved to a Q point from the P point by the X axis robot 109. In addition, the movement from the P point to the Q point is a movement that is parallel to the X axis. Finally, the head unit 107 is moved to an R point serving as an mount point of the electronic components by the X axis robot 109 and the Y axis robots 111a and 111b. Imaging of the electronic components sucked by the head unit 107 using the 3D sensor 113 is intermittently performed from when the head unit 107 is located at the P point to when the head unit 107 is located at the Q point.

FIG. 25 is a diagram that illustrates a variation with time of the speed in the X axis direction and the speed in the Y axis direction when the head unit 107 illustrated in FIG. 23 is moved. As illustrated in FIG. 25, the head unit 107 reaching the P point from the O point is accelerated toward the Q point, then, is moved by a predetermined distance at a constant speed, and is decelerated toward and until reaching the Q point. As mentioned above, imaging of the electronic component using the 3D sensor 113 is performed from when the head unit 107 is located at the P point to when the head unit 107 is located at the Q point. That is, the imaging control using the control unit 135 included in the electronic component mounting apparatus of the present embodiment is not limited while the head unit 107 is moved at a constant speed from the P point to the Q point. The control unit 135 controls the 3D sensor 113 so as to perform imaging while the head unit 107 is accelerated from the P point toward the Q point, and controls the 3D sensor 113 so as to perform imaging while the head unit 107 is decelerated toward and until reaching the Q point.

In FIG. 25, the variation with time of the speed in the X axis direction and the speed in the Y axis direction when the imaging timing is limited while the head unit 107 is moved at a constant speed from the P point to the Q point is indicated by a broken line. In this case, the head unit 107 is moved from the O point to a p point illustrated in FIG. 24, is accelerated toward a direction parallel to the X axis from the p point, is moved at a constant speed from the P point to the Q point, and is decelerated toward reaching a q point illustrated in FIG. 24. Finally, the head unit 107 is moved from the q point to the R point.

In a case illustrated by a broken line in FIG. 25, although the acceleration time from the p point to the P point and the deceleration time from the Q point to the q point are included in a time during which it is possible to perform imaging, in the second example, the acceleration time is also included in the imaginable time. For this reason, when comparing the movement time from the O point to the R point of the head unit 107, the movement time of an example indicated by a solid line in FIG. 25 is shorter than a case of being indicated by the broken line in FIG. 25. As a result, the takt time in the electronic component mounting apparatus of the present embodiment can be optimized.

In addition, since the signal from the encoders 131 and 133 indicates a predetermined position, until the control unit 135 instructs the lighting of the LED light 153 and the exposure of the imaging element, although the time also depends on the processing capability of the control unit 135, for example, 30μ seconds are required. If the movement speed of the head unit 107 is 1,000 mm/second, the delay (deviation in the movement direction of the head unit 107) as the image of 30 μm occurs. When imaging is performed while the head unit 107 is accelerated as in the present example, the imaging timing determination unit 205 of the control unit 135 determines the imaging timing that cancels the delay, while calculating the delay depending on the movement speed of the head unit 107.

THIRD EXAMPLE

FIG. 26 is a diagram that illustrates the movement route in a third example until the head unit 107 sucks the electronic components from the feeder unit 103 and mounts the electronic components onto the substrate 115. An O point illustrated in FIG. 26 indicates a central position of the head unit 107 when sucking the small electronic components. The head unit 107 sucks the electronic components at the O point and then is moved to the P point by the X axis robot 109 and the Y axis robots 111a and 111b. Next, the head unit 107 is moved to the Q point from the P point by the X axis robot 115 and the Y axis robots 111a and 111b. In addition, the movement from the P point to the Q point is a movement that is oblique to the X axis and is close to the substrate 109 on the Y axis. Finally, the head unit 107 is moved to the R point serving as an mount point of the electronic components by the X axis robot 109 and the Y axis robots 111a and 111b. Imaging of the small electronic components sucked by the head unit 107 is intermittently performed when the head unit 107 passes through the 3D sensor 113 while the head unit 107 is moved from the P point to the Q point.

FIG. 27 is a diagram that illustrates a variation with time of the speed in the X axis direction and the speed in the Y axis direction when the head unit 107 illustrated in FIG. 26 is moved. As illustrated in FIG. 27, the head unit 107 reaching the P point from the O point is accelerated toward the Q point, then, is moved by a predetermined distance at a constant speed, and is decelerated toward and until reaching to the Q point. As mentioned above, imaging of the small electronic component using the 3D sensor 113 is intermittently performed when the head unit 107 passes through the 3D sensor 113. In the present example, the imaging timing is determined depending on the position on the Y axis illustrated by the Y axis encoder signal.

FIGS. 28 to 31 illustrate a vertical positional relationship between the visual fields 171a and 171b and the head unit 107 for each imaging timing of the electronic components using the 3D sensor 113. In the present example, when the kinds of the small electronic components sucked by the head unit 107 in which the nozzles are formed in two lines are different from each other for each line, the imaging timings of the small electronic components 121a and 121b are each delayed, and are set to the different lighting forms at each imaging timing. In addition, when the head unit 107 sucks the electronic component of one kind, the imaging timings of the electronic components of each line may be the same.

In FIG. 27, the variation with time of the speed in the X axis direction and the speed in the Y axis direction is illustrated by a broken line when the head unit 107 is moved in parallel to the X axis while imaging the electronic components. In the example illustrated by the broken line in FIG. 27, an amount of movement of the head unit 107 in the Y axis direction during imaging is 0. That is, the amount of movement is identical to the case illustrated in FIG. 24 in the second example. However, in the third example, at the time of the movement from the P point to the Q point including the imaging time, the head unit 107 is also moved toward the substrate 115 in the Y axis direction. That is, the rate of movement of the head unit 107 on the Y-axis is controlled during the time up to the mount point (R point). For this reason, when comparing the movement time from the O point to the R point of the head unit 107, the movement time according to the present example illustrated by the solid line in FIG. 27 is shorter than the case illustrated by the broken line in FIG. 27. As a result, the takt timing in the electronic component mounting apparatus of the present embodiment can be optimized. In addition, the present example can also be applied to a case where the head unit 107 sucks the small electronic components.

FOURTH EXAMPLE

FIG. 32 is a diagram that illustrates each timing of the light emission of an LED light 153, the output of the image data of the imaging element, and writing of the image data to a video memory 213 when recognizing the electronic component sucked to the head unit 107 based on a three-dimensional image. In the example illustrated in FIG. 32, lights of different lighting forms are each irradiated to the two small electronic components sucked to the different lines of the head unit 107 in which the nozzles are formed in two lines at the different timings. Thus, the imaging elements of each camera included in the 3D sensor 113 are exposed in synchronization with each lighting. The image data obtained by the exposure of the imaging element is sequentially transmitted to the video memory 213 of the component recognition unit 137 included in the electronic component mounting apparatus of the present embodiment. FIG. 33 is a diagram that illustrates each timing of the light emission of the LED light 153 and writing of the image data to the video memory 213 when the head unit 107 is moved in the X axis direction and the operations of FIG. 32 are performed several times.

FIG. 34 is a diagram that illustrates each timing of the light emission of an LED light 153, the output of the image data of the imaging element, and writing of the image data to the video memory 213 when recognizing the electronic component sucked to the head unit 107 based on a two-dimensional image. In the example illustrated in FIG. 34, lights of different lighting forms are each irradiated to the two small electronic components sucked to the different lines of the head unit 107 in which the nozzles are formed in two lines at the different timings. Thus, the imaging elements of the center camera 151C included in the 3D sensor 113 are exposed in synchronization with each lighting. The image data obtained by the exposure of the imaging element is sequentially transmitted to the video memory 213 of the component recognition unit 137 included in the electronic component mounting apparatus of the present embodiment. FIG. 35 is a diagram that illustrates each timing of the light emission of the LED light 153 and writing of the image data to the video memory 213 when the head unit 107 is moved in the X axis direction and the operations of FIG. 34 are performed several times.

FIG. 36 is a diagram that illustrates an example of each timing of the light emission of the LED light 153 and writing of the image data to the video memory 213 when the head unit 107 is moved in the X axis direction and the operation illustrated in FIG. 32 or the operation illustrated in FIG. 35 is selectively performed. In the example illustrated in FIG. 36, the control unit 135 included in the electronic component mounting apparatus of the present embodiment selects whether the recognition of the electronic component sucked to the head unit 107 is performed based on the three-dimensional image or is performed based on the two-dimensional image depending on the kinds of the electronic components or the like. The imaging control unit 207 of the control unit 135 controls so as to expose the imaging elements 165a and 165b of the center camera 151C of the 3D sensor 113 when imaging the two-dimensional image, and controls so as to expose each of all the imaging elements included in the center camera 151C, the left camera 151L and the right camera 151R of the 3D sensor 113 when imaging the three-dimensional image. The component recognition based on the three-dimensional image includes, for example, a lead floating inspection of QFP, an inspection of an adsorption posture of a minute component or the like.

As illustrated in FIGS. 32 to 36, a total size of the image data written to the video memory 213 when imaging the two-dimensional image is smaller than a total size of the image data written to the video memory 213 when imaging the three-dimensional image. That is, regarding an amount of data transmitted from the 3D sensor 113 to the video memory 213 per one imaging, the case of the two-dimensional image is smaller than the case of the three-dimensional image. Furthermore, in order to generate the three-dimensional image, the image processing unit 215 needs to perform the 3D processing of the image data from each camera. For this reason, regarding the processing burden due to the software or the hardware of the component recognition unit 137, this becomes greater in the case of the three-dimensional image along with an increase in amount of processing data, compared to the two-dimensional image. In other words, the processing burden of the component recognition unit 137 is small when recognizing based on the two-dimensional image.

As mentioned above, in the fourth example, depending on whether there is a need for a two-dimensional image or there is a need for a three-dimensional image as the image used in the recognition of the electronic components, the imaging control unit 207 of the control unit 135 controls the imaging form of the 3D sensor 113 for each electronic component sucked by the head unit 107, for each electronic component group, or for each kind of electronic component. In this manner, by selectively and properly using the imaging forms, the transmission of the unnecessary image data does not occur, and unnecessary burden is not applied to the component recognition unit 137. As a result, the electronic component mounting apparatus is able to rapidly recognize the components.

The electronic component mounting apparatus related to the present invention is useful as a mounting apparatus or the like that mounts the electronic components on the substrate.

DESCRIPTION OF REFERENCE NUMERALS AND SIGNS 100 electronic component mounting apparatus
101 main body
103 feeder unit
105 tray supply unit
107, 107S, 107L head unit
109 X axis robot
111a, 111b Y axis robot
113 three-dimensional sensor (3D sensor)
115 substrate
117 belt
119 nozzle
121 electronic component
131, 133 encoder
135 control unit
137 component recognition unit
151C center camera
151L left camera
151R right camera
153 LED light
165a, 165b, 165c, 165d, 165e, 165f imaging element
161 telecentric lens
163 beam splitter
167c, 167d, 167e, 167f lens
171a, 171b visual field
201 encoder I/F unit
203 position determination unit
205 imaging timing determination unit
207 imaging control unit
209 lighting control unit
211 image data I/F unit
213 video memory
215 image processing unit
121a, 121b small electronic component
121c large electronic component

What is claimed is:

1. An electronic component mounting apparatus comprising:
   a substrate conveyance mechanism unit configured to convey a substrate with an electronic component mounted thereon in a first direction;
   a component supply unit configured to supply the electronic component;
   a holding unit configured to hold the electronic component supplied from the component supply unit;
   a movement mechanism unit configured to move the holding unit;
   a component imaging unit configured to image the electronic component that is held by the holding unit;
   a control unit configured to control an imaging form of the electronic components by the component imaging unit; and
   a component recognition unit configured to recognize the electronic component based on an image that is imaged by the component imaging unit,
   wherein the component imaging unit has an area camera that includes at least one imaging element, and
   the control unit controls the component imaging unit so as to image the electronic component that is held by the holding unit, when the holding unit is moved in a direction oblique to the first direction and close to the substrate by the movement mechanism unit.

2. The electronic component mounting apparatus according to claim 1, wherein the control unit controls the component imaging unit so as to image the electronic component held by the holding unit while the holding unit is moved at a constant speed.

3. The electronic component mounting apparatus according to claim 1,
   wherein the component imaging unit has a component lighting unit that lights the electronic component that is held by the holding unit during imaging, and
   when the holding unit holds a first electronic component and a second electronic component of different kinds, the control unit delays imaging timing of the first electronic component by the imaging element and imaging timing of the second electronic component by the imaging element, respectively, and changes the lighting form due to the component lighting unit at each imaging timing.

4. An electronic component mounting apparatus comprising:
   a substrate conveyance mechanism unit configured to convey a substrate with an electronic component mounted thereon in a first direction;
   a component supply unit configured to supply the electronic component;
   a holding unit configured to hold the electronic component supplied from the component supply unit;
   a movement mechanism unit configured to move the holding unit;
   a component imaging unit configured to image the electronic component that is held by the holding unit;
   a control unit configured to control an imaging form of the electronic component by the component imaging unit; and
   a component recognition unit configured to recognize the electronic component based on an image that is imaged by the component imaging unit,
   wherein the component imaging unit has at least three area cameras that include at least one imaging element, and visual fields of the imaging element are common to each other regardless of the area camera, and the control unit controls the component imaging unit so as to image the electronic component that is held by the holding unit, when the holding unit is moved in a direction oblique to the first direction and close to the substrate by the movement mechanism unit.

5. The electronic component mounting apparatus according to claim 4, wherein the control unit controls the component imaging unit so as to image the electronic component held by the holding unit while the holding unit is moved at a constant speed.

6. The electronic component mounting apparatus according to claim 4,
   wherein the component imaging unit has a component lighting unit that lights the electronic component that is held by the holding unit during imaging, and
   when the holding unit holds a first electronic component and a second electronic component of different kinds, the control unit delays imaging timing of the first electronic component by the imaging element of each area camera and imaging timing of the second electronic component by the imaging element of each area camera, respectively, and changes the lighting form due to the component lighting unit at each imaging timing.

7. An electronic component mounting method performed by an electronic component mounting apparatus comprising:
   a substrate conveyance mechanism unit configured to convey a substrate with an electronic component mounted thereon in a first direction;
   a component supply unit configured to supply the electronic component;
   a holding unit configured to hold the electronic component supplied from the component supply unit;
   a movement mechanism unit configured to move the holding unit;
   a component imaging unit configured to image the electronic component that is held by the holding unit;
   a control unit configured to control an imaging form of the electronic component by the component imaging unit; and
   a component recognition unit configured to recognize the electronic component based on an image that is imaged by the component imaging unit, the component imaging unit having at least three area cameras that include at least one imaging element, and visual fields of the imaging element being common to each other regardless of the area camera, the electronic component mounting method comprises:
   a step of controlling the component imaging unit so as to image the electronic component that is held by the holding unit, when the holding unit is moved in a direction oblique to the first direction and close to the substrate by the movement mechanism unit.

8. The electronic component mounting apparatus according to claim 1, wherein the area camera comprises a first imaging element and a second imaging element which are independent devices having different visual fields,
   the control unit sets the imaging form of the component imaging unit to a first imaging mode or a second imaging mode according to a size of the electronic component,
   when the imaging form is set to the first imaging mode, the component recognition unit recognizes a first electronic component that is held by the holding unit based on an image imaged by the first imaging element, and the component recognition unit also recognizes a second electronic component that is held by the holding unit together with the first electronic component based on an image imaged by the second imaging element,
   when the imaging form is set to the second imaging mode, the component recognition unit recognizes an electronic component that is held by the holding unit based on an image obtained by combining an image imaged by the first imaging element and an image imaged by the second imaging element, and
   the control unit controls the first imaging element and the second imaging element independently so as to image the electronic component held by the holding unit.

9. The electronic component mounting apparatus according to claim 4, wherein each of the area cameras comprises a first imaging element and a second imaging element which are independent devices having different visual fields,
   the control unit sets the imaging form of the component imaging unit to a first imaging mode or a second imaging mode according to a size of the electronic component,
   when the imaging form is set to the first imaging mode, the component recognition unit recognizes a first electronic component that is held by the holding unit based on an image imaged by the first imaging element of each of the area cameras, and the component recognition unit also recognizes a second electronic component that is held by the holding unit together with the first electronic component based on an image imaged by the second imaging element of each of the area cameras,
   when the imaging form is set to the second imaging mode, the component recognition unit recognizes an electronic component that is held by the holding unit based on an image obtained by combining an image imaged by the first imaging element of each of the area cameras and an image imaged by the second imaging element of each of the area cameras, and
   the control unit controls the first imaging element and the second imaging element independently so as to image the electronic component held by the holding unit.

10. The electronic component mounting method according to claim 7, wherein each of the area cameras comprises a first imaging element and a second imaging element which are independent devices having different visual fields,
    the control unit sets the imaging form of the component imaging unit to a first imaging mode or a second imaging mode according to a size of the electronic component,
    when the imaging form is set to the first imaging mode, the component recognition unit recognizes a first electronic component that is held by the holding unit based on an image imaged by the first imaging element of each of the area cameras, and the component recognition unit also recognizes a second electronic component that is held by the holding unit together with the first electronic component based on an image imaged by the second imaging element of each of the area cameras,
    when the imaging form is set to the second imaging mode, the component recognition unit recognizes an electronic component that is held by the holding unit based on an image obtained by combining an image imaged by the first imaging element of each of the area cameras and an image imaged by the second imaging element of each of the area cameras, and
    the control unit controls the first imaging element and the second imaging element independently so as to image the electronic component held by the holding unit.

* * * * *